US010751411B2

(12) United States Patent
Jacobs, Jr. et al.

(10) Patent No.: US 10,751,411 B2
(45) **Date of Patent: *Aug. 25, 2020**

(54) RECOMBINANT HERPES SIMPLEX VIRUS 2 (HSV-2) VACCINE VECTORS

(71) Applicant: ALBERT EINSTEIN COLLEGE OF MEDICINE, Bronx, NY (US)

(72) Inventors: William Jacobs, Jr., Pelham, NY (US); Pablo A. Gonzalez Munoz, Santiago-Chile (CL); Betsy Herold, Rowayton, CT (US); Christopher Petro, Pleasanton, CA (US)

(73) Assignee: ALBERT EINSTEIN COLLEGE OF MEDICINE, INC., Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/526,056

(22) Filed: Jul. 30, 2019

(65) Prior Publication Data

US 2020/0023058 A1 Jan. 23, 2020

Related U.S. Application Data

(63) Continuation of application No. 15/995,471, filed on Jun. 1, 2018, now Pat. No. 10,391,165, which is a continuation of application No. 15/015,322, filed on Feb. 4, 2016, now Pat. No. 9,999,665, which is a continuation-in-part of application No. PCT/US2015/018272, filed on Mar. 2, 2015.

(60) Provisional application No. 62/080,663, filed on Nov. 17, 2014, provisional application No. 61/946,965, filed on Mar. 3, 2014.

(51) Int. Cl.

| | |
|---|---|
| ***A61K 39/245*** | (2006.01) |
| ***A61K 39/12*** | (2006.01) |
| ***C12N 7/00*** | (2006.01) |
| ***C07K 14/005*** | (2006.01) |
| ***A61K 39/00*** | (2006.01) |

(52) U.S. Cl.

CPC ............ *A61K 39/245* (2013.01); *A61K 39/12* (2013.01); *C07K 14/005* (2013.01); *C12N 7/00* (2013.01); *A61K 2039/525* (2013.01); *A61K 2039/5254* (2013.01); *A61K 2039/5256* (2013.01); *A61K 2039/54* (2013.01); *A61K 2039/572* (2013.01); *C12N 2710/16621* (2013.01); *C12N 2710/16622* (2013.01); *C12N 2710/16634* (2013.01); *C12N 2710/16643* (2013.01); *C12N 2710/16662* (2013.01); *C12N 2710/16671* (2013.01)

(58) Field of Classification Search

CPC .............. A61K 2039/505; A61K 39/12; A61K 2039/5258; A61K 2039/5254; A61K 2039/6075; A61K 35/763; A61K 39/245; A61K 39/42; C07K 14/005; C12N 7/00; C12N 15/86; C12N 2710/16622; C12N 2710/16634

See application file for complete search history.

(56) References Cited

U.S. PATENT DOCUMENTS

| | | | | |
|---|---|---|---|---|
| 4,810,634 | A | 3/1989 | Post | |
| 9,284,355 | B2 | 3/2016 | Friedman et al. | |
| 2005/0053605 | A1 | 3/2005 | Betz et al. | |
| 2008/0089910 | A1 | 4/2008 | Visalli et al. | |
| 2009/0246227 | A1 | 10/2009 | Friedman et al. | |
| 2010/0330112 | A1 | 12/2010 | Long et al. | |
| 2011/0039729 | A1 | 2/2011 | Delisa et al. | |
| 2012/0219579 | A1 | 8/2012 | Yusibov et al. | |
| 2016/0158343 | A1* | 6/2016 | Jacobs, Jr. ........... | C07K 14/005 424/186.1 |

FOREIGN PATENT DOCUMENTS

| | | | |
|---|---|---|---|
| CN | 101288770 | A | 10/2008 |
| EP | 0139417 | A1 | 5/1985 |
| JP | 2008-507784 | A | 8/1996 |
| NZ | 204948 | A | 10/1987 |
| WO | 0144477 | A1 | 6/2001 |
| WO | 2005/005637 | A2 | 1/2005 |
| WO | 2005005637 | A2 | 1/2005 |
| WO | 2006004878 | A1 | 1/2006 |
| WO | 2008/030560 | A2 | 3/2008 |
| WO | 2008030560 | A2 | 3/2008 |

OTHER PUBLICATIONS

Kimberlin DM. Chapter 75: Immunotherapy of HSV Infections—antibody delivery. In: Arvin A, Campadelli-Fiume G, Mocarski E, et al., editors. Human Herpesviruses: Biology, Therapy, and Immunoprophylaxis. Cambridge: Cambridge University Press; 2007. Chapter 75. https://www.ncbi.nlm.nih.gov/books/NBK47389/.*

European Search Report received for EP Application No. 15758673, dated Sep. 27, 2017.

Van Lint et al., Immunization with a replication-defective herpes simplex virus 2 mutant reduces herpes simplex virus 1 infection and prevents ocular disease, Virology, Elsevier, Amsterdam, NL, vol. 368, No. 2, dated Oct. 29, 2007, pp. 227-231.

Awasthi et al: "An HSV-1 gD mutant virus as an entry-impaired live virus vaccine", Vaccine, Elsevier, Amsterdam, NL, vol. 26, No. 9, dated Jan. 14, 2008, pp. 1195-1203.

Brans R et al: "Prevention of Genital Herpes Simplex Virus Type 1 and 2 Disease in Mice Immunized with a gD-Expressing Dominant-Negative Recombinant HSV-1", The Journal of Investigative Dermatology : Official Journal of the Society for Investigative Dermatology and the European Society for Dermatological Research, Elsevier, US, vol. 129, No. 10, dated Oct. 1, 2009, pp. 2470-2479.

Sita Awasthi et al: "Live Attenuated Herpes Simplex Virus 2 Glycoprotein E Deletion Mutant as a Vaccine Candidate Defective in Neuronal Spread", Journal of Virology., vol. 86, No. 8, dated Feb. 8, 2012, pp. 4586-4598.

(Continued)

*Primary Examiner* — Rachel B Gill

(74) *Attorney, Agent, or Firm* — Cantor Colburn LLP

(57) ABSTRACT

Recombinant herpes simplex virus 2 (HSV-2) vaccine vectors, virions thereof, compositions and vaccines comprising such, and methods of use thereof are each provided.

9 Claims, 14 Drawing Sheets

Specification includes a Sequence Listing.

(56) References Cited

OTHER PUBLICATIONS

McLean C S et al: "Induction of a protective immune response by mucosal vaccination with a DISC HSV-1 vaccine", Vaccine, Elsevier, Amsterdam, NL, vol. 14, No. 10, dated Jul. 1, 1996, pp. 987-992.
Arun V Iyer et al: "Single dose of Glycoprotein K (gK)-deleted HSV-1 live-attenuated virus protects mice against lethal vaginal challange with HSV-1 and HSV-2 and induces lasting T cell memory immune responses", Virology Journal, vol. 10, No. 1, dated Jan. 1, 2013, p. 317.
Xavier J. Da Costa et al: "Immunization against Genital Herpes with a Vaccine Virus That has Defects in Productive and Latent Infection", Proceedings of the National Academy of Sciences of the United States of America, dated Jun. 8, 1999, pp. 6994-6998.
Chinese First Office Action issued in Application No. 2015800222226, dated Dec. 13, 2018.
Japanese Preliminary Notice of Reasons for Rejection issued in Application No. 2016-555659, dated Jan. 29, 2019.
Cheshenko N. et al., FASEB J., 28(7)(2013), p. 2584-2599.
Meseda C. A. et al., Virology, 318(2004), p. 420-428.
Communication Supplementary European Search Report dated Sep. 27, 2017 in connection with European Patent Application No. 15756673.6.
Argnani R, Lufino M, Manservigi M, Manservigi R. Replication-competent herpes simplex vectors: design and applications. Gene Ther. Oct. 2005; 12 Suppl 1:S170-7.
Johnston C, Koelle DM, Wald A. HSV-2: in pursuit of a vaccine. The Journal of Clinical Investigation. 2011;121(12):4600-4609. doi.10.1172/JCI57148.
Cheshenko N, Trepanier JB, Stefanidou M, Buckley N, Gonzalez P, Jacobs W, Herold BC. HSV activates Akt to trigger calcium release and promote viral entry: novel candidate target for treatment and supression. FASEB J. Jul. 2013;27(7):2584-99.
Rauch DA, Rodriguez N, Roller RJ. Mutations in herpes simplex virus glycoproteins D distinguish entry of free virus from cell-cell spread. J Virol. Dec. 2000;74(24):11437-46.
Dropulic LK, Cohen JI. The challange of developing a herpes simplex virus 2 vaccine. Expert Rev Vaccines, Dec. 2012;11 (12):1429-40.
Office Action dated Nov. 14, 2017 in connection with U.S. Appl. No. 15/455,495.
Chiang HY, Cohen GH, Eisenberg RJ. Identification of functional regions of herpes simplex virus glycoprotein gD by using linker-insertion mutagenesis. J Virol. Apr. 1994;68(4):2529-43.
Bolland S et al., entitled "Virology: Ups and downs in the search for a Herpes simplex virus vaccine," eLife 2015;4:e06863. DOI: 10.7554/elife.06883, 3 pages.
Van Lint A L et al., entitled "Immunization with a replication-defective herpes simplex virus 2 mutant reduces herpes simplex virus 1 infection and prevents ocular disease," Virology 366 (2007) 227-231.
Awasthi S et al., entitled "An HSV-1 gD mutant virus as an entry-impaired live virus vaccine", Vaccine (2008) 26, 1195-1203.
Brans R et al., entitled "Prevention of Genital Herpes Simplex Virus Type 1 and 2 Disease in Mice Immunized with a gD-Expressing Dominant-Negative Recombinant HSV-1," Journal of Investigative Dermatology (2009), vol. 129, 2470-2479.
Awasthi S et al, entitled "Live Attenuated Herpes Simplex Virus 2 Glycoprotein E Deletion Mutant as a Vaccine Candidate Defective in Neuronal Spread," Journal of Virology, Apr. 2012, vol. 86, No. 8, 4586-4598.
McLean C S et al., entitled "Induction of a protective immune response by mucosal vaccination with a DISC HSV-1 vaccine," Vaccine, 1996, vol. 14, No. 10, 987-992.
Lyer A V et al., entitled "Single dose of Glycoprotein K (gK)-deleted HSV-1 live-attenuated virus protects mice against lethal vaginal challange with HSV-1 and HSV-2 and induces lasting T cell memory immune responses." Virology Journal, 2013, 10:317, 11 pages.
Da Costa, X J et al., entitled "Immunization against genital herpes with a vaccine virus that has defects in productive and latent infection," Proc. Natl. Acad. Sci, vol. 96, pp. 6994-6998, Jun. 1999.
PCT International Search Report and Written Opinion, dated Aug. 10, 2015 in connection with PCT International Application No. PCT/US2015/18272, 17 pages.
Ligas M W et al., entitled "A Herpes Simplex Virus Mutant in Which Glycoprotein D Sequences are Replaced by β-Galactosidase Sequences Binds to but is Unable to Penetrate into Cells," Journal of Virology, May 1986, p. 1486-1494.
Belshe et al. "Efficacy results of a trial of a herpes simplex vaccine," New England Journal of Medicine, 5:366(1), pp. 34-43, Jan. 5, 2012.
Jiang et al. "Preventing neonatal herpes infections through maternal immunization," Future Virology, 12 (12):709-711, Dec. 2017.
Yorty et al. "Transplacental Transfer and Subsequent Neonate Utilization of Herpes Simplex Virus-Specific Immunity Are Resilient to Acute Maternal Stress," Journal of Virology, 77 (12): 6613-6619, Jun. 2003.

* cited by examiner

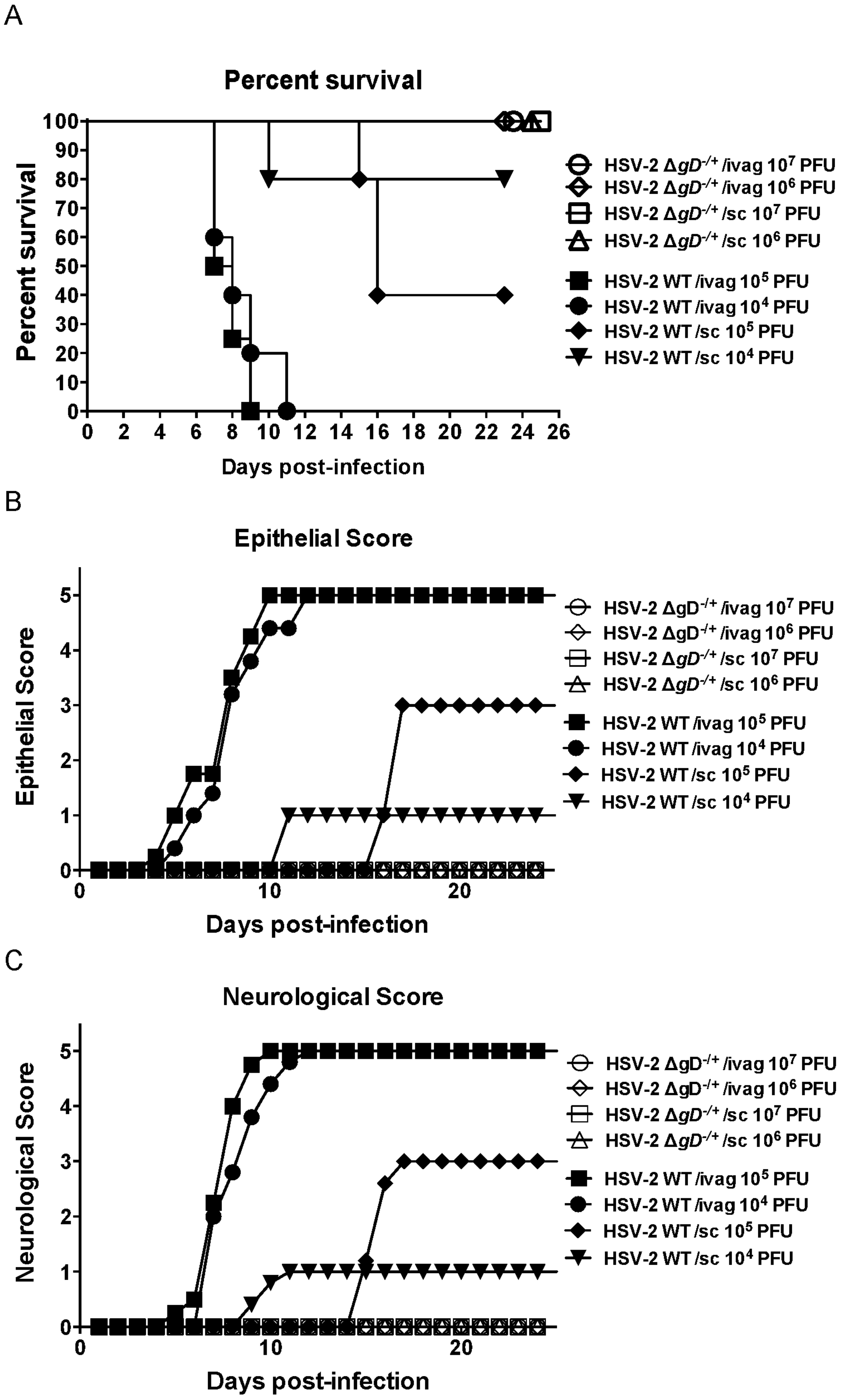
Fig. 2A-C

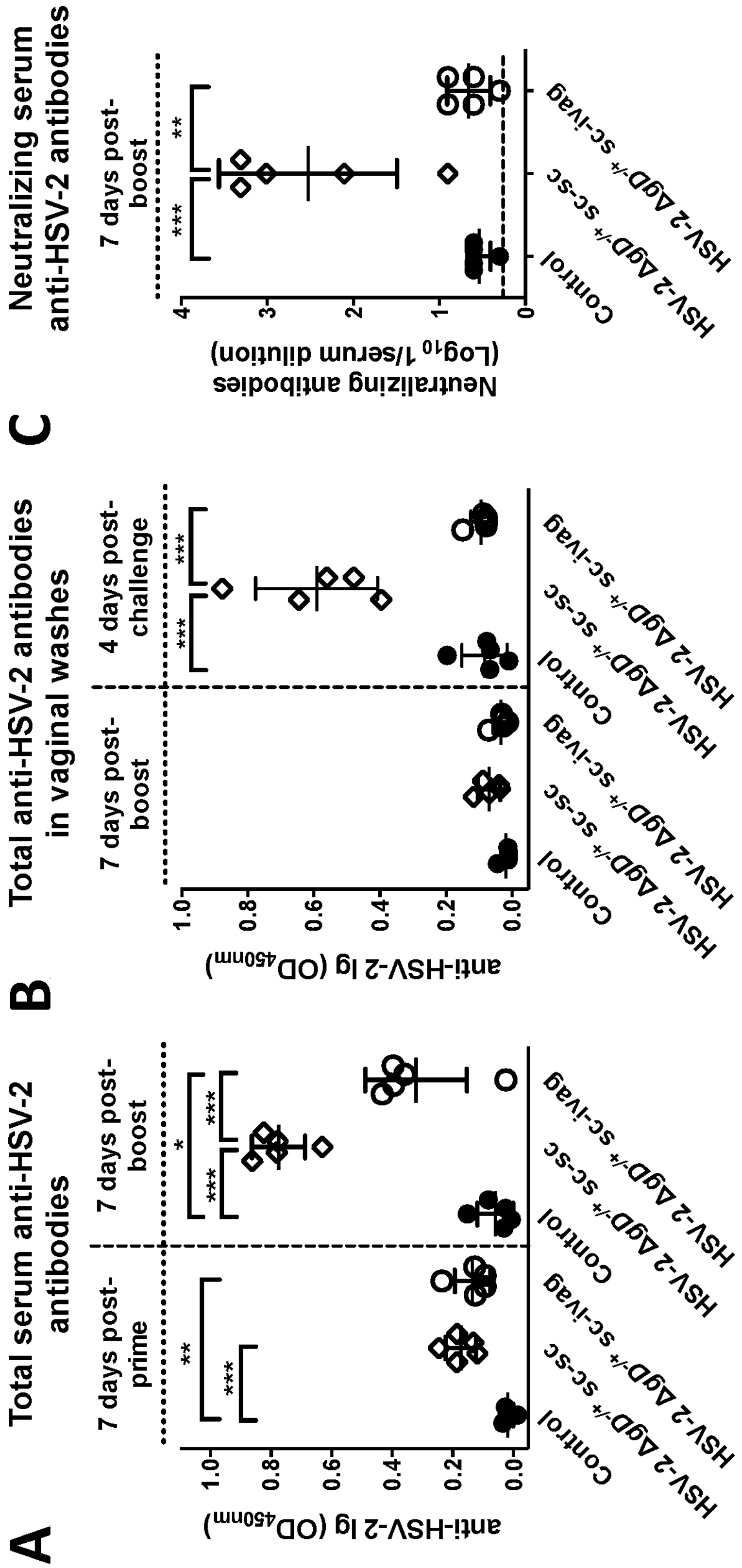
Fig. 3A-C

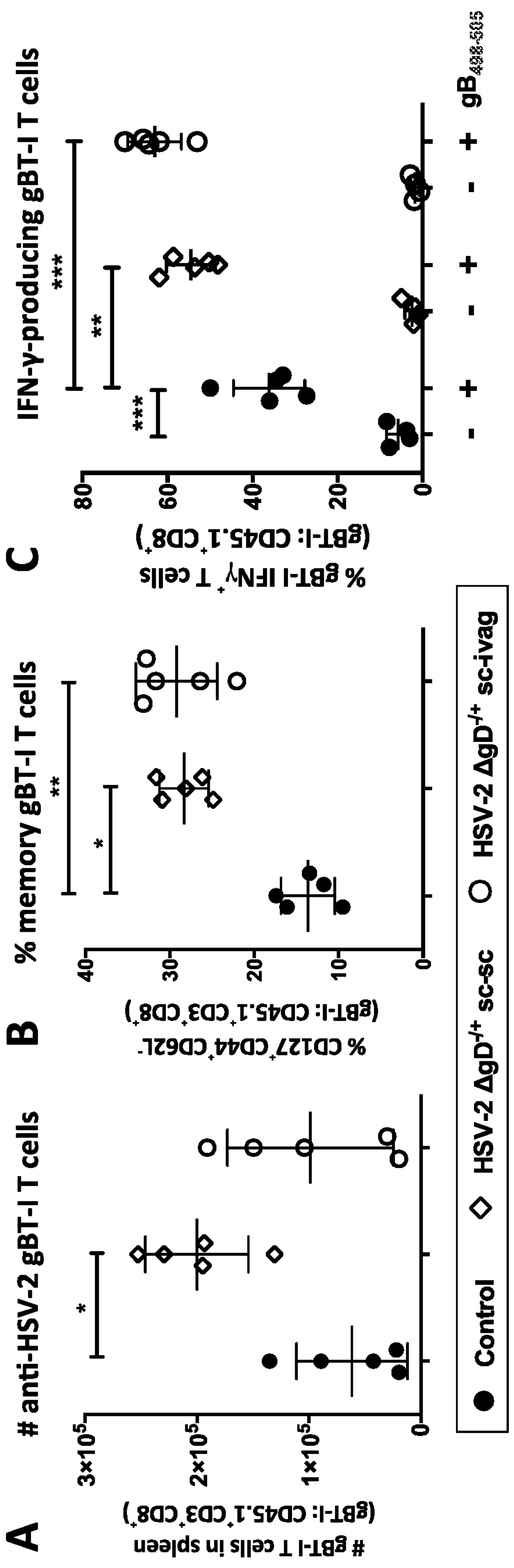
Fig. 4A-C

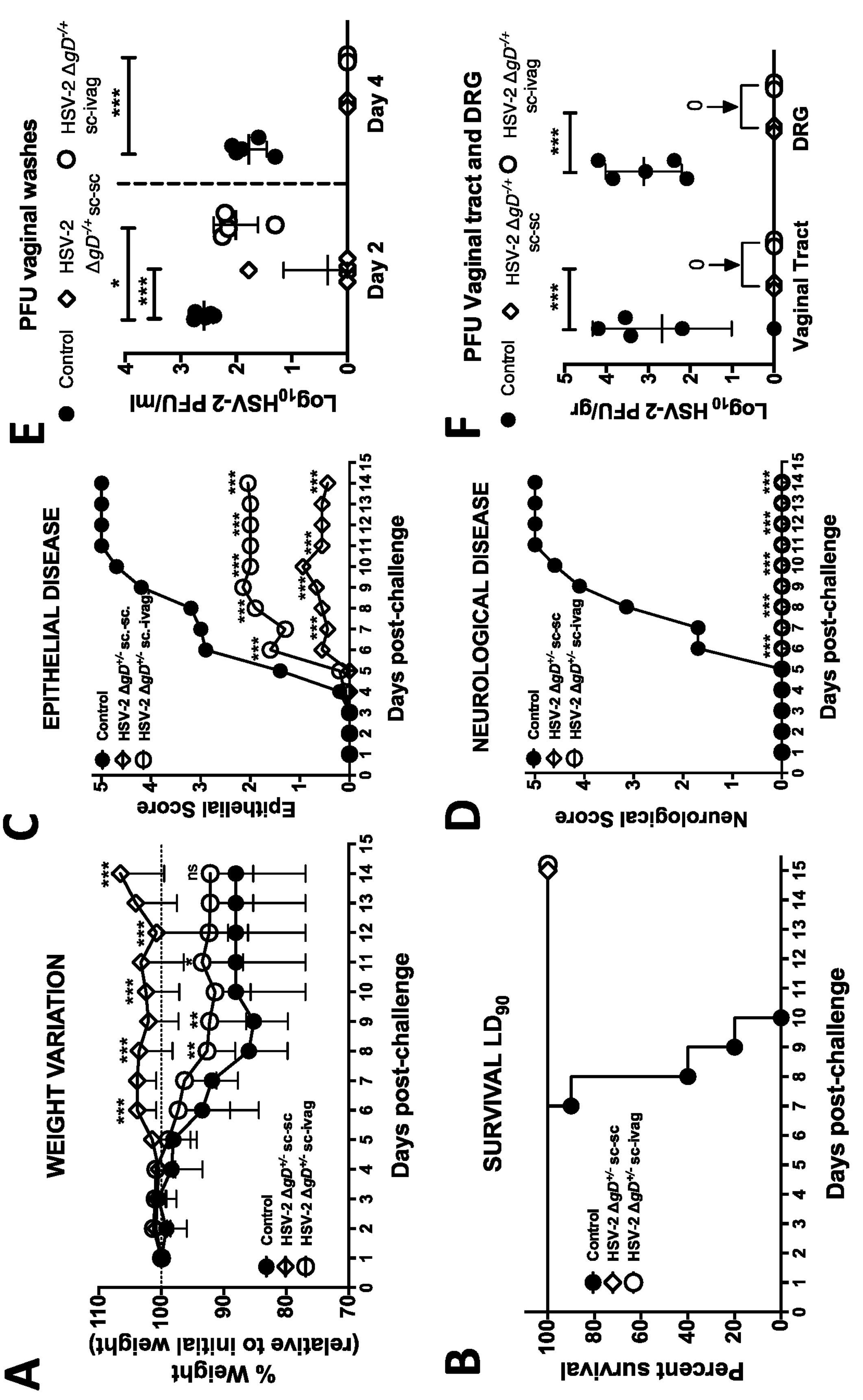
Fig. 5A-F

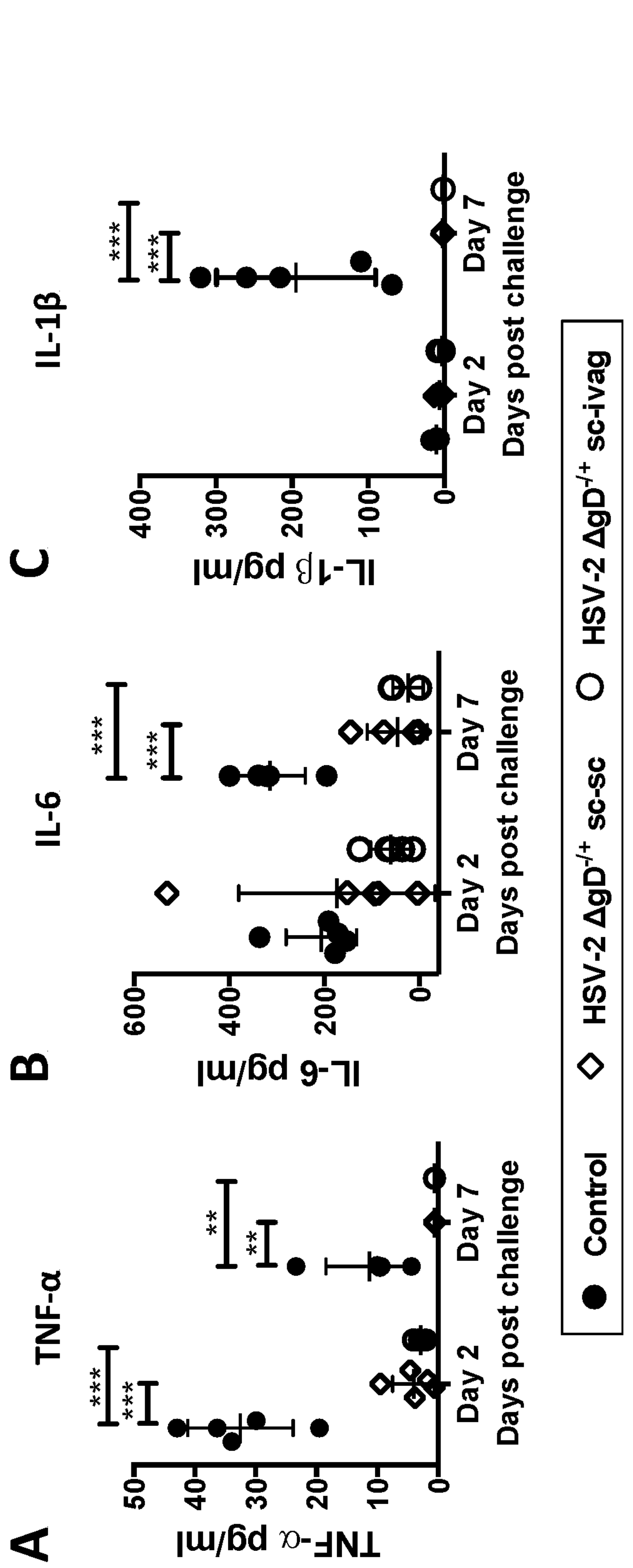
Fig. 6A-C

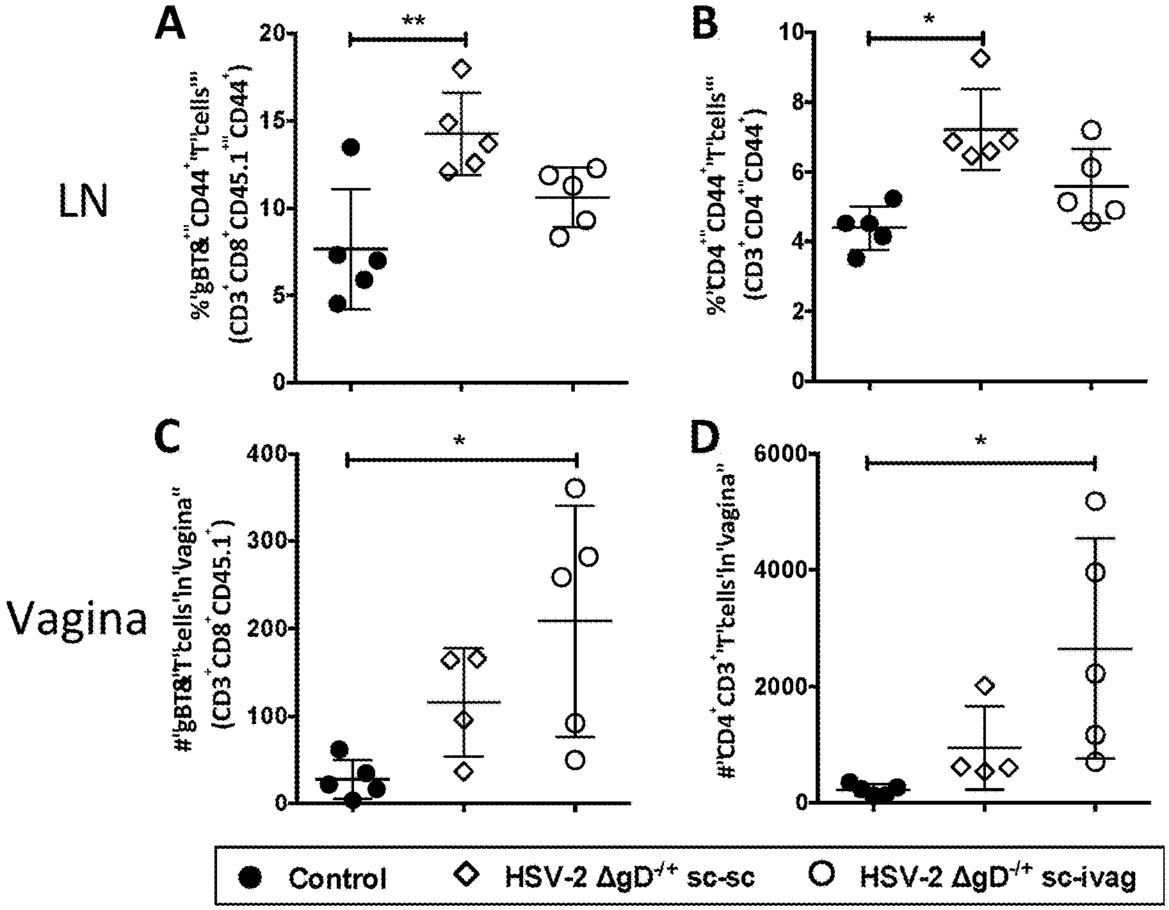
Fig 7A-D

SEQUENCE LISTING

```
<160> NUMBER OF SEQ ID NOS: 2

<210> SEQ ID NO 1
<211> LENGTH: 393
<212> TYPE: PRT
<213> ORGANISM: Herpes Simplex Virus - 2

<400> SEQUENCE: 1

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240
```

Ser Ile Gly Met Leu Pro Arg Phe Ile Pro Glu Asn Gln Arg Thr Val
245 250 255

Ala Leu Tyr Ser Leu Lys Ile Ala Gly Trp His Gly Pro Lys Pro Pro
260 265 270

Tyr Thr Ser Thr Leu Leu Pro Pro Glu Leu Ser Asp Thr Thr Asn Ala
275 280 285

Thr Gln Pro Glu Leu Val Pro Glu Asp Pro Glu Asp Ser Ala Leu Leu
290 295 300

Glu Asp Pro Ala Gly Thr Val Ser Ser Gln Ile Pro Pro Asn Trp His
305 310 315 320

Ile Pro Ser Ile Gln Asp Val Ala Pro His His Ala Pro Ala Ala Pro
325 330 335

Ser Asn Pro Gly Leu Ile Ile Gly Ala Leu Ala Gly Ser Thr Leu Ala
340 345 350

Val Leu Val Ile Gly Gly Ile Ala Phe Trp Val Arg Arg Arg Ala Gln
355 360 365

Met Ala Pro Lys Arg Leu Arg Leu Pro His Ile Arg Asp Asp Asp Ala
370 375 380

Pro Pro Ser His Gln Pro Leu Phe Tyr
385 390

<210> SEQ ID NO 2
<211> LENGTH: 394
<212> TYPE: PRT
<213> ORGANISM: Herpes Simplex Virus - 1

<400> SEQUENCE: 2

Met Gly Gly Ala Ala Ala Arg Leu Gly Ala Val Ile Leu Phe Val Val
1 5 10 15

Ile Val Gly Leu His Gly Val Arg Gly Lys Tyr Ala Leu Ala Asp Ala
20 25 30

Ser Leu Lys Met Ala Asp Pro Asn Arg Phe Arg Gly Lys Asp Leu Pro
35 40 45

Val Leu Asp Gln Leu Thr Asp Pro Pro Gly Val Arg Arg Val Tyr His
50 55 60

Ile Gln Ala Gly Leu Pro Asp Pro Phe Gln Pro Pro Ser Leu Pro Ile
65 70 75 80

Thr Val Tyr Tyr Ala Val Leu Glu Arg Ala Cys Arg Ser Val Leu Leu
85 90 95

Asn Ala Pro Ser Glu Ala Pro Gln Ile Val Arg Gly Ala Ser Glu Asp
100 105 110

Val Arg Lys Gln Pro Tyr Asn Leu Thr Ile Ala Trp Phe Arg Met Gly
115 120 125

Gly Asn Cys Ala Ile Pro Ile Thr Val Met Glu Tyr Thr Glu Cys Ser
130 135 140

Tyr Asn Lys Ser Leu Gly Ala Cys Pro Ile Arg Thr Gln Pro Arg Trp
145 150 155 160

Asn Tyr Tyr Asp Ser Phe Ser Ala Val Ser Glu Asp Asn Leu Gly Phe
165 170 175

Leu Met His Ala Pro Ala Phe Glu Thr Ala Gly Thr Tyr Leu Arg Leu
180 185 190

Val Lys Ile Asn Asp Trp Thr Glu Ile Thr Gln Phe Ile Leu Glu His
195 200 205

Arg Ala Lys Gly Ser Cys Lys Tyr Ala Leu Pro Leu Arg Ile Pro Pro

-continued

```
    210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro Lys Ala Pro
            260                 265                 270

Tyr Thr Ser Thr Leu Leu Pro Pro Glu Leu Ser Glu Thr Pro Asn Ala
        275                 280                 285

Thr Gln Pro Glu Leu Ala Pro Glu Asp Pro Glu Asp Ser Ala Leu Leu
    290                 295                 300

Glu Asp Pro Val Gly Thr Val Ala Pro Gln Ile Pro Pro Asn Trp His
305                 310                 315                 320

Ile Pro Ser Ile Gln Asp Ala Ala Thr Pro Tyr His Pro Pro Ala Thr
                325                 330                 335

Pro Asn Asn Met Gly Leu Ile Ala Gly Ala Val Gly Gly Ser Leu Leu
            340                 345                 350

Ala Ala Leu Val Ile Cys Gly Ile Val Tyr Trp Met Arg Arg Arg Thr
        355                 360                 365

Gln Lys Ala Pro Lys Arg Ile Arg Leu Pro His Ile Arg Glu Asp Asp
    370                 375                 380

Gln Pro Ser Ser His Gln Pro Leu Phe Tyr
385                 390
```

RECOMBINANT HERPES SIMPLEX VIRUS 2 (HSV-2) VACCINE VECTORS

CROSS-REFERENCE TO RELATED APPLICATIONS

This application is a continuation of U.S. patent application Ser. No. 15/995,471, filed Jun. 1, 2018, which is a continuation of U.S. patent application Ser. No. 15/015,322, filed Feb. 4, 2016, which is a continuation-in-part of PCT International Application PCT/US2015/018272, filed Mar. 2, 2015, which claims benefit of U.S. Provisional Application No. 61/946,965, filed Mar. 3, 2014, and of U.S. Provisional Application No. 62/080,663, filed Nov. 17, 2014, the contents of all of which are hereby incorporated by reference.

STATEMENT OF GOVERNMENT SUPPORT

This invention was made with government support under grant numbers AI061679, AI51519, AI097548, AI026170 and AI065309 awarded by the National Institutes of Health. The government has certain rights in the invention.

BACKGROUND OF THE INVENTION

Throughout this application various publications are referred to, including by number in square brackets. Full citations for these references may be found at the end of the specification. The disclosures of these publications, and all patents, patent application publications and books referred to herein, are hereby incorporated by reference in their entirety into the subject application to more fully describe the art to which the subject invention pertains.

Herpes simplex virus types 1 and 2 (HSV-1 and HSV-2) persist as significant health problems globally, disproportionally impacting developing countries and poor communities around the world and fueling the HIV epidemic. Vaccines are urgently needed for these infections as currently there is no effective vaccine for HSV-1, HSV-2 or HIV. HSV-1 is the primary cause of infectious blindness, while HSV-2 is the primary cause of genital ulcers globally, although HSV-1 is now more commonly identified in association with genital tract disease in developed countries. Genital herpes is a recurrent, lifelong disease that can stigmatize and psychologically impacts those affected. Infection with HSV-2 significantly increases the likelihood of acquiring and transmitting HIV, while vertical transmission of either serotype often leads to severe infant morbidity or death. Recent clinical trials of HSV-2 vaccines based on sub-unit formulations using viral glycoproteins D alone or in combination with glycoprotein B (gD and gB) have failed, despite inducing systemic neutralizing antibodies. Surprisingly an HSV-2 gD subunit (gD-2) vaccine provided partial protection against HSV-1, but no protection against HSV-2. Several attenuated viruses been evaluated pre-clinically, but clinical studies to date have been limited to therapeutic applications (reducing frequency of recurrences) and have also failed to show efficacy. Thus, novel vaccine strategies must be engineered and evaluated.

The present invention addresses this need for new and improved HSV-1 and HSV-2 vaccines.

SUMMARY OF THE INVENTION

An isolated, recombinant herpes simplex virus-2 (HSV-2) is provided having a deletion of an HSV-2 glycoprotein D-encoding gene ($U_{s6}$) in the genome thereof.

Also provided is a virion of an isolated, recombinant HSV-2 having a deletion of an HSV-2 glycoprotein D-encoding gene ($U_{s6}$) in the genome thereof.

An isolated cell is provided comprising therein a recombinant HSV-2 genome as described herein or a recombinant HSV-1 gene as described herein, wherein the cell is not present in a human being.

Also provided is a vaccine composition comprising the recombinant HSV-2 virus as described herein, or the virion as described herein.

Also provided is a composition comprising the recombinant HSV-2 virus as described herein, or the virion as described herein, wherein the genome of the virus or virion comprises at least a deletion of a second gene, wherein the second gene is necessary for HSV-2 viral replication or virulence.

A pharmaceutical composition comprising the recombinant HSV-2 virus as described herein, or the virion as described herein, and a pharmaceutically acceptable carrier.

Also provided is a method of eliciting an immune response in a subject comprising administering to the subject an amount of (i) the recombinant HSV-2 virus as described herein; (ii) a virion thereof as described herein, (iii) the vaccine as described herein; (iv) a composition as described herein; or (v) a pharmaceutical composition as described herein, in an amount effective to elicit an immune response in a subject.

Also provided is a method of treating an HSV-1, HSV-2 or HSV-1 and HSV-2 co-infection in a subject or treating a disease caused by an HSV-1, HSV-2 or co-infection in a subject comprising administering to the subject an amount of (i) the recombinant HSV-2 virus as described herein; (ii) a virion thereof as described herein, (iii) the vaccine as described herein; (iv) a composition as described herein; or (v) a pharmaceutical composition as described herein, in an amount effective to treat an HSV-1, HSV-2 or co-infection or treat a disease caused by an HSV-1, HSV-2 or co-infection in a subject.

Also provided is a method of vaccinating a subject for HSV-1, HSV-2 or co-infection comprising administering to the subject an amount of (i) the recombinant HSV-2 virus as described herein; (ii) a virion thereof as described herein, (iii) the vaccine as described herein; (iv) a composition as described herein; or (v) a pharmaceutical composition as described herein, in an amount effective to vaccinate a subject for HSV-1, HSV-2 or co-infection.

Also provided is a method of immunizing a subject against HSV-1, HSV-2 or co-infection comprising administering to the subject an amount of (i) the recombinant HSV-2 virus as described herein; (ii) a virion thereof as described herein, (iii) the vaccine as described herein; (iv) a composition as described herein; or (v) a pharmaceutical composition as described herein, in an amount effective to immunize a subject against HSV-1, HSV-2 or co-infection.

In an embodiment of the vaccines, compositions and pharmaceutical compositions, and of the methods of use thereof, the amount of recombinant HSV-2 is an amount of pfu of recombinant HSV-2 effective to achieve the stated aim.

Also provided is a method of producing a virion of a recombinant herpes simplex virus-2 (HSV-2), having a deletion of an HSV-2 glycoprotein D-encoding gene in the genome thereof and comprising a HSV-1 or HSV-2 glycoprotein D on a lipid bilayer thereof, comprising infecting a cell comprising a heterologous nucleic acid encoding a HSV-1 or HSV-2 glycoprotein D with a recombinant herpes simplex virus-2 (HSV-2) having a deletion of an HSV-2 glycoprotein D-encoding gene in the genome thereof under conditions permitting replication of the recombinant herpes simplex virus-2 (HSV-2) and recovering a HSV-2 virion produced by the cells.

Also provided is a recombinant nucleic acid having the same sequence as a genome of a wild-type HSV-2 except that the recombinant nucleic acid does not comprise a sequence encoding an HSV-2 glycoprotein D.

Also provided is an isolated, recombinant herpes simplex virus-2 (HSV-2) having a deletion of an HSV-2 glycoprotein D-encoding gene in the genome thereof for treating or preventing an HSV-1, HSV-2 or co-infection in a subject.

Also provided is a virion of an isolated, recombinant HSV-2 having a deletion of an HSV-2 glycoprotein D-encoding gene in the genome thereof for treating or preventing an HSV-1, HSV-2 or co-infection in a subject.

An isolated, recombinant herpes simplex virus-2 (HSV-2) is provided having a deletion of an HSV-2 glycoprotein D-encoding gene in the genome thereof.

Also provided is a virion of an isolated, recombinant HSV-2 having a deletion of an HSV-2 glycoprotein D-encoding gene in the genome thereof.

Also provided is an isolated cell comprising therein a virus as described herein or a virion as described herein, wherein the cell is not present in a human being.

A vaccine composition comprising a virus as described herein, or a virion as described herein.

Also provided is a composition comprising a virus as described herein, or a virion as described herein, wherein the genome of the virus or virion comprises at least a deletion of a second gene, wherein the second gene is necessary for HSV-2 viral replication.

Also provided is pharmaceutical composition comprising a virus as described herein, or a virion as described herein, and a pharmaceutically acceptable carrier.

Also provided is a method of eliciting an immune response in a subject comprising administering to the subject an amount of (i) a virus as described herein; (ii) a virion as described herein, (iii) a vaccine as described herein; (iv) a composition as described herein; or (v) a pharmaceutical composition as described herein, in an amount effective to elicit an immune response in a subject.

Also provided is a method of treating an HSV-2 infection in a subject or treating a disease caused by an HSV-2 infection in a subject comprising administering to the subject an amount of (i) a virus as described herein; (ii) a virion as described herein, (iii) a vaccine as described herein; (iv) a composition as described herein; or (v) a pharmaceutical composition as described herein, in an amount effective to treat an HSV-2 infection or treat a disease caused by an HSV-2 infection in a subject.

Also provided is a method of vaccinating a subject for HSV-2 infection comprising administering to the subject an amount of (i) a virus as described herein; (ii) a virion as described herein, (iii) a vaccine as described herein; (iv) a composition as described herein; or (v) a pharmaceutical composition as described herein, in an amount effective to vaccinate a subject for HSV-2.

Also provided is a method of immunizing a subject against HSV-2 infection comprising administering to the subject an amount of (i) a virus as described herein; (ii) a virion as described herein, (iii) a vaccine as described herein; (iv) a composition as described herein; or (v) a pharmaceutical composition as described herein, in an amount effective to immunize a subject against HSV-2.

Also provided is a method of producing a virion of a recombinant herpes simplex virus-2 (HSV-2), having a deletion of an HSV-2 glycoprotein D-encoding gene in the genome thereof and comprising an HSV-1 glycoprotein D on a lipid bilayer thereof, comprising infecting a cell comprising a heterologous nucleic acid encoding a HSV-1 glycoprotein D with a recombinant herpes simplex virus-2 (HSV-2) having a deletion of an HSV-2 glycoprotein D-encoding gene in the genome thereof under conditions permitting replication of the recombinant herpes simplex virus-2 (HSV-2) and recovering a recombinant HSV-2 virion comprising an HSV-1 glycoprotein D on a lipid bilayer thereof produced by the cell.

Also provided is a method of producing a virion of a recombinant herpes simplex virus-2 (HSV-2), having a deletion of an HSV-2 glycoprotein D-encoding gene in the genome thereof and comprising a non-HSV-2 surface glycoprotein on a lipid bilayer thereof, comprising infecting a cell comprising a heterologous nucleic acid encoding the non-HSV-2 surface glycoprotein with a recombinant herpes simplex virus-2 (HSV-2) having a deletion of an HSV-2 glycoprotein D-encoding gene in the genome thereof under conditions permitting replication of the recombinant herpes simplex virus-2 (HSV-2) and recovering a recombinant HSV-2 virion comprising a non-HSV-2 surface glycoprotein on a lipid bilayer thereof produced by the cell.

Also provided is a recombinant nucleic acid is provided having the same sequence as a genome of a HSV-2 except that the sequence does not comprise a sequence encoding an HSV-2 glycoprotein D.

Also provided is an isolated, recombinant herpes simplex virus-2 (HSV-2) having a deletion of an HSV-2 glycoprotein D-encoding gene in the genome thereof for treating or preventing an HSV-2 infection in a subject.

Also provided is an isolated, recombinant herpes simplex virus-2 (HSV-2) having a deletion of an HSV-2 glycoprotein D-encoding gene in the genome thereof for treating or preventing an HSV-1 infection in a subject.

Also provided is a virion of an isolated, recombinant HSV-2 having a deletion of an HSV-2 glycoprotein D-encoding gene in the genome thereof for treating or preventing an HSV-2 infection in a subject.

Also provided is a method of treating an HSV-1 infection, or HSV-1 and HSV-2 co-infection, in a subject, or treating a disease caused by an HSV-2 infection or HSV-1 and HSV-2 co-infection in a subject comprising administering to the subject an amount of (i) a virus as described herein; (ii) a virion as described herein, (iii) a vaccine as described herein; (iv) a composition as described herein; or (v) a pharmaceutical composition as described herein, in an amount effective to treat an HSV-2 infection or treat a disease caused by an HSV-2 infection in a subject or an amount effective to treat an HSV-1 and HSV-2 co-infection or treat a disease caused by an HSV-1 and HSV-2 co-infection in a subject.

Also provided is a method of vaccinating a subject for an HSV-1 infection, or HSV-1 and HSV-2 co-infection, comprising administering to the subject an amount of (i) a virus as described herein; (ii) a virion as described herein, (iii) a vaccine as described herein; (iv) a composition as described herein; or (v) a pharmaceutical composition as described herein, in an amount effective to vaccinate a subject for an HSV-1 infection, or HSV-1 and HSV-2 co-infection.

Also provided is a method of immunizing a subject against an HSV-1 infection, or HSV-1 and HSV-2 co-infection, comprising administering to the subject an amount of (i) a virus as described herein; (ii) a virion as described herein, (iii) a vaccine as described herein; (iv) a composition as described herein; or (v) a pharmaceutical composition as described herein, in an amount effective to immunize a subject against an HSV-1 infection, or HSV-1 and HSV-2 co-infection.

Also provided is an isolated, recombinant herpes simplex virus-2 (HSV-2) having a deletion of an HSV-2 glycoprotein D-encoding gene in the genome thereof and further comprising a heterogenous antigen of a pathogen.

Also provided is a method of inducing antibody dependent cell mediated cytotoxicity (ADCC) against an antigenic target in a subject comprising administering to the subject an isolated, recombinant herpes simplex virus-2 (HSV-2) having a deletion of an HSV-2 glycoprotein D-encoding gene in the genome thereof and further comprising a heterogenous antigen on a lipid bilayer thereof in an amount effective to induce antibody dependent cell mediated cytotoxicity (ADCC) against an antigenic target.

BRIEF DESCRIPTION OF THE DRAWINGS

FIG. 2A-C: A. Severe combined immunodeficiency (SCID) mice inoculated with up to $10^7$ plaque-forming units (pfu) of HSV-2 ΔgD−/+ virus do not manifest signs of disease after high dose intravaginal or subcutaneous inoculation. In contrast SCID mice inoculated with wild-type virus at a 1,000-fold lower viral dose ($10^4$ pfu) succumb to disease. Survival curves are shown in A, epithelial scores (scale of 0 to 5) for evidence of erythema, edema, or genital ulcers in B and neurological scores (scale of 0 to 5) for evidence of neuronal infection in C.

FIG. 3A-C: Immunization with HSV-2 ΔgD−/+ virus elicits anti-HSV-2 antibodies. While sc.-sc. immunization elicits significant levels of both systemic and mucosal (vaginal washes) anti-HSV-2 antibodies, sc.-i.vag. immunization with HSV-2 ΔgD−/+ elicits lower levels of systemic anti-HSV-2 antibodies and no increase in antibody levels in vaginal washes. Anti-HSV-2 antibody levels in serum are shown in A and anti-HSV-2 antibody levels in vaginal washes are shown in B. Mice immunized with ΔgD−/+ display neutralizing anti-HSV-2 antibodies in the serum after challenge with virulent HSV-2. The neutralizing capacity of the antibodies elicited by ΔgD−/+ immunization is shown in C. (* p<0.05; p<0.01; *p<0.001).

FIG. 4A-C: A: CD8+ gBT-I T cell counts in spleens of C57Bl/6 mice transferred with Tg T cells, then primed and boosted with HSV-2 ΔgD−/+ or VD60 lysate (Control). B: Percentage of gBT-I memory T cells in spleens of vaccinated or Control mice. C: 14 days after boost, splenocytes were isolated and re-stimulated in vitro with gB498-505 peptide and analyzed 6 hr later for cytokine production by intracellular cytokine staining and flow cytometry. (*p<0.05; p<0.01; *p<0.001).

FIG. 5A-F: Immunization with HSV-2 ΔgD−/+($10^6$ pfu/mouse) protects mice from a lethal HSV-2 challenge. Mice were primed subcutaneously and boosted 3-weeks apart either sc. or i.vag. and then challenged 3-weeks after boost intravaginally with an $LD_{90}$ of virulent wild-type HSV-2 (4674). While Control (immunized with the VD60 cell lysate) mice succumbed to disease, as manifested by significant weight loss (A) and death (B), ΔgD−/+-immunized mice displayed significantly less pathology. Furthermore, ΔgD−/+-immunized mice showed less epithelial disease (C) and neurological pathology (D) after lethal challenge. Additionally, ΔgD−/+-vaccinated mice displayed significantly less viral loads in vaginal washes (E), vaginal tissue and dorsal root ganglia (DRG) (F) after intravaginal challenge with a lethal dose of virulent HSV-2 compared to mice immunized with VD60 cell lysate as a Control. No infectious virus could be recovered from ΔgD−/+-immunized mice in Day 4 vaginal washes or Day 5 vaginal tissue and DRG. (*p<0.05; p<0.01; *p<0.001).

FIG. 6A-C: Mice immunized with HSV-2 ΔgD−/+ secrete less inflammatory cytokines in vaginal washes after challenge with virulent HSV-2. Mice immunized with HSV-2 ΔgD−/+ secrete less TNF-α, IL-6 and IL-1β in vaginal washes than mice immunized with VD60 lysate and challenged with virulent HSV-2. Differences in inflammatory cytokine expression are observed at different time-points after challenge. (*p<0.05; p<0.01; *p<0.001).

FIG. 7A-D: Immunization with HSV-2 ΔgD−/+ recruits T cells to the infection site and associated LNs. Mice immunized sc.-sc. with ΔgD−/+ displayed increased percentages of activated anti-HSV-2 gBT-I CD8+(A) and CD4+ T cells (B) in sacral lymph nodes (LNs) after challenge with virulent HSV-2. LNs were extracted and incubated 6 h with UV-inactivated ΔgD−/− and then stained with antibodies for flow cytometry analysis. Mice immunized sc.-i.vag. with ΔgD−/+ displayed increased numbers of anti-HSV-2 gBT-I CD8+(C) and CD4+ T cells (D) in the vagina after challenge with virulent HSV-2. Vaginal tissues were processed to extract T cells and stained with antibodies for flow cytometry analysis. Cell counting was done with (CountBright™, Lifetechnologies). (*p<0.05; **p<0.01).

DETAILED DESCRIPTION OF THE INVENTION

Figure 1:
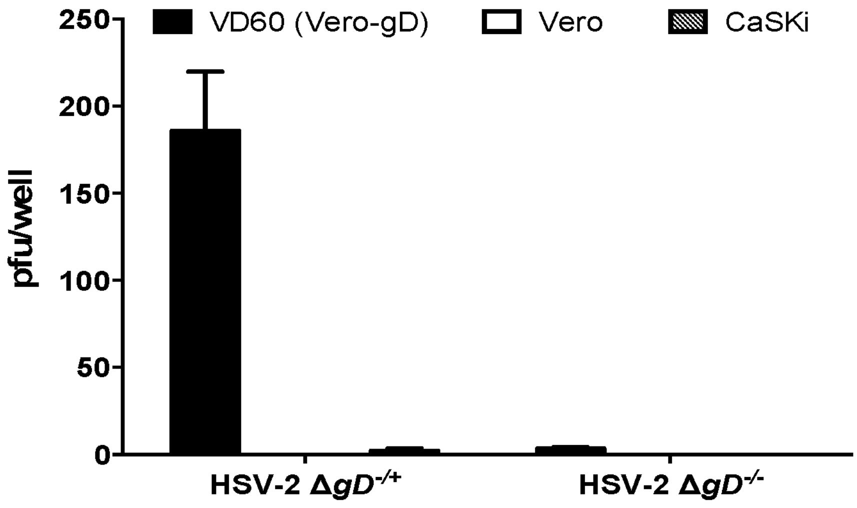
FIG. 1: HSV-2 ΔgD initiates an abortive infection: HSV-2 ΔgD−/+ only replicates successfully in cells that provide gD in trans (e.g. VD60 [40, 41]), but not in cells such as Vero cells (ATCC CCL-81, Green monkey kidney) or CaSki (ATCC CRL-1550, *Homo sapiens*, cervix) that do not encode $U_S6$. Non-complemented HSV-2 ΔgD (ΔgD−/− obtained from Vero cells) cannot infect cells such as Vero and CaSki, which do not encode $U_{S6}$.

An isolated, recombinant herpes simplex virus-2 (HSV-2) is provided having a deletion of an HSV-2 glycoprotein D-encoding gene in the genome thereof.

In an embodiment, the HSV-2 glycoprotein D comprises the amino acid sequence set forth in SEQ ID NO:1:

```
MGRLTSGVGTAALLVVAVGLRVVCAKYALADPSLKMADPNRFRGKNLPVL
DQLTDPPGVKRVYHIQPSLEDPFQPPSIPITVYYAVLERACRSVLLHAPS
EAPQIVRGASDEARKHTYNLTIAWYRMGDNCAIPITVMEYTECPYNKSLG
VCPIRTQPRWSYYDSFSAVSEDNLGFLMHAPAFETAGTYLRLVKINDWTE
ITQFILEHRARASCKYALPLRIPPAACLTSKAYQQGVTVDSIGMLPRFIP
ENQRTVALYSLKIAGWHGPKPPYTSTLLPPELSDTTNATQPELVPEDPED
SALLEDPAGTVSSQIPPNWHIPSIQDVAPHHAPAAPSNPGLIIGALAGST
LAVLVIGGIAFWVRRRAQMAPKRLRLPHIRDDDAPPSHQPLFY (HSV-
2 reference strain HG52)
```

In an embodiment, the isolated, recombinant HSV-2 further comprises a herpes simplex virus-1 (HSV-1) glycoprotein D on a lipid bilayer thereof.

In an embodiment, the HSV-1 glycoprotein D comprises the amino acid sequence set forth in SEQ ID NO:2:

```
MGGAAARLGAVILFVVIVGLHGVRGKYALADASLKMADPNRFRGKDLPVL
DQLTDPPGVRRVYHIQAGLPDPFQPPSLPITVYYAVLERACRSVLLNAPS
EAPQIVRGASEDVRKQPYNLTIAWFRMGGNCAIPITVMEYTECSYNKSLG
ACPIRTQPRWNYYDSFSAVSEDNLGFLMHAPAFETAGTYLRLVKINDWTE
ITQFILEHRAKGSCKYALPLRIPPSACLSPQAYQQGVTVDSIGMLPRFIP
ENQRTVAVYSLKIAGWHGPKAPYTSTLLPPELSETPNATQPELAPEDPED
SALLEDPVGTVAPQIPPNWHIPSIQDAATPYHPPATPNNMGLIAGAVGGS
LLAALVICGIVYWMRRRTQKAPKRIRLPHIREDDQPSSHQPLFY
(HSV-1 reference strain F)
```

In an embodiment, the HSV-2 glycoprotein D-encoding gene is an HSV-2 $U_{S6}$ gene. (For example, see Dolan et al. *J Virol.* 1998 March; 72(3): 2010-2021. (PMCID: PMC109494) "The Genome Sequence of Herpes Simplex Virus Type 2" for HSV-2 genome and $U_{S6}$ gene, hereby incorporated by reference in its entirety).

In an embodiment, the HSV-2 in which the HSV-2 glycoprotein D-encoding gene is deleted is an HSV-2 having a genome (prior to the deletion) as set forth in one of the following Genbank listed sequences: HSV-2(G) (KU310668), HSV-2(4674) (KU310667), B3x1.1 (KU310657), B3x1.2 (KU310658), B3x1.3 (KU310659), B3x1.4 (KU310660), B3x1.5 (KU310661), B3x2.1 (KU310662), B3x2.2 (KU310663), B3x2.3 (KU310664), B3x2.4 (KU310665), B3x2.5 (KU310666).

Also provided is a virion of an isolated, recombinant HSV-2 having a deletion of an HSV-2 glycoprotein D-encoding gene in the genome thereof.

In an embodiment, the virion further comprises an HSV-1 or HSV-2 glycoprotein D on a lipid bilayer thereof. In an embodiment, the HSV-2 glycoprotein D-encoding gene is an HSV-2 $U_{S6}$ gene. In an embodiment, the virion further comprises an HSV-1 glycoprotein D on a lipid bilayer thereof.

In an embodiment, the virus further comprises an HSV-1 or HSV-2 glycoprotein D on a lipid bilayer thereof. In an embodiment, the HSV-2 glycoprotein D-encoding gene is an HSV-2 $U_{S6}$ gene. In an embodiment, the virus further comprises an HSV-1 glycoprotein D on a lipid bilayer thereof.

An isolated cell is provided comprising therein a recombinant HSV-2 genome which does not comprise an HSV-2 $U_{S6}$ gene.

In an embodiment, the recombinant HSV-2 genome is recombinant by virtue of having had a HSV-2 glycoprotein D gene deleted therefrom.

In an embodiment, the cell is a complementing cell which provides expressed HSV 1 or 2 glycoprotein not encoded for by the recombinant HSV-2 genome. In an embodiment, the complementing cell comprises a heterologous nucleic acid encoding a HSV-1 or HSV-2 glycoprotein D. In an embodiment, the cell expresses HSV-1 glycoprotein D on a membrane thereof. In an embodiment of the cell, the HSV-1 glycoprotein D is encoded by the heterologous nucleic acid, which heterologous nucleic acid is a HSV-1 or HSV-2 glycoprotein D gene, or is a nucleic acid having a sequence identical to a HSV-1 or HSV-2 glycoprotein D gene.

Also provided is a vaccine composition comprising the recombinant HSV-2 virus as described herein, or the virion as described herein. In an embodiment, the vaccine comprises an immunological adjuvant. In an embodiment, the vaccine does not comprise an immunological adjuvant. In an embodiment of the vaccine, compositions or pharmaceutical compositions described herein comprising a recombinant HSV-2, the HSV-2 is live.

Also provided is a composition comprising the recombinant HSV-2 virus as described herein, or the virion as described herein, wherein the genome of the virus or virion comprises at least a deletion of a second gene, wherein the second gene is necessary for HSV-2 viral replication or virulence.

A pharmaceutical composition comprising the recombinant HSV-2 virus as described herein, or the virion as described herein, and a pharmaceutically acceptable carrier.

In an embodiment, the composition or pharmaceutical composition or vaccine is formulated so that it is suitable for subcutaneous administration to a human subject. In an embodiment, the composition or pharmaceutical composition or vaccine is formulated so that it is suitable for intravaginal administration to a human subject. In an embodiment, the composition or pharmaceutical composition or vaccine is formulated so that it is suitable for intra-muscular, intra-nasal, or mucosal administration to a human subject.

Also provided is a method of eliciting an immune response in a subject comprising administering to the subject an amount of (i) the recombinant HSV-2 virus as described herein; (ii) a virion thereof as described herein, (iii) the vaccine as described herein; (iv) a composition as described herein; or (v) a pharmaceutical composition as described herein, in an amount effective to elicit an immune response in a subject.

Also provided is a method of treating an HSV-2 infection in a subject or treating a disease caused by an HSV-1, HSV-2 or co-infection in a subject comprising administering to the subject an amount of (i) the recombinant HSV-2 virus as described herein; (ii) a virion thereof as described herein, (iii) the vaccine as described herein; (iv) a composition as described herein; or (v) a pharmaceutical composition as described herein, in an amount effective to treat an HSV-1, HSV-2 or co-infection or treat a disease caused by an HSV-1, HSV-2 or co-infection in a subject. In an embodiment, the methods comprise treating an HSV-1 or HSV-2 pathology caused by an HSV-1, HSV-2 or co-infection. In an embodiment of the methods, the disease caused by an HSV-1, HSV-2 or co-infection is a genital ulcer. In an embodiment of the methods, the disease caused by an HSV-1, HSV-2 or co-infection is herpes, oral herpes, herpes whitlow, genital herpes, eczema herpeticum, herpes gladiatorum, HSV keratitis, HSV retinitis, HSV encephalitis or HSV meningitis.

In an embodiment of the methods herein regarding treating, or vaccinating for, an HSV-1, HSV-2 or co-infection (i.e. infection with both HSV-1 and HSV-2), separate, individual, embodiments of treating an HSV-1 infection, treating an HSV-2 infection, treating a co-infection, vaccinating against an HSV-1 infection, vaccinating against an HSV-2 infection, and vaccinating against a co-infection, are each provided.

Also provided is a method of vaccinating a subject for HSV-1, HSV-2 or co-infection comprising administering to the subject an amount of (i) the recombinant HSV-2 virus as described herein; (ii) a virion thereof as described herein, (iii) the vaccine as described herein; (iv) a composition as described herein; or (v) a pharmaceutical composition as described herein, in an amount effective to vaccinate a subject for HSV-1, HSV-2 or co-infection.

Also provided is a method of immunizing a subject against HSV-1, HSV-2 or co-infection comprising administering to the subject an amount of (i) the recombinant HSV-2 virus as described herein; (ii) a virion thereof as described herein, (iii) the vaccine as described herein; (iv) a composition as described herein; or (v) a pharmaceutical composition as described herein, in an amount effective to immunize a subject against HSV-1, HSV-2 or co-infection.

In an embodiment of the methods, the subject is administered a subcutaneous or intravaginal priming dose and is administered a second dose subcutaneously or intravaginally. In an embodiment of the methods, the subject is administered as many subcutaneous or intravaginal priming doses to elicit anti-HSV antibodies and T cells.

Also provided is a method of producing a virion of a recombinant herpes simplex virus-2 (HSV-2), having a deletion of an HSV-2 glycoprotein D-encoding gene in the genome thereof and comprising an HSV-1 or HSV-2 glycoprotein D on a lipid bilayer thereof, comprising infecting a cell comprising a heterologous nucleic acid encoding a HSV-1 or HSV-2 glycoprotein D with a recombinant herpes simplex virus-2 (HSV-2) having a deletion of an HSV-2 glycoprotein D-encoding gene in the genome thereof under conditions permitting replication of the recombinant herpes simplex virus-2 (HSV-2) and recovering a HSV-2 virion produced by the cell.

In an embodiment, the cell expresses HSV-1 or HSV-2 glycoprotein D on a membrane thereof.

Also provided is a recombinant nucleic acid having the same sequence as a genome of a wild-type HSV-2 except that the recombinant nucleic acid does not comprise a sequence encoding an HSV-2 glycoprotein D. In an embodiment, the recombinant nucleic acid is a DNA. In an embodiment, the recombinant nucleic acid is an RNA.

Also provided is an isolated, recombinant herpes simplex virus-2 (HSV-2) having a deletion of an HSV-2 glycoprotein D-encoding gene in the genome thereof for treating or preventing an HSV-1, HSV-2 or co-infection in a subject. In an embodiment, the isolated, recombinant HSV-2 further comprises a herpes simplex virus-1 (HSV-1) or herpes simplex virus-2 (HSV-2) glycoprotein D on a lipid bilayer thereof. In an embodiment of the isolated, recombinant HSV-2, the HSV-2 glycoprotein D-encoding gene is an HSV-2 US6 gene.

Also provided is a virion of an isolated, recombinant HSV-2 having a deletion of an HSV-2 glycoprotein D-encoding gene in the genome thereof for treating or preventing an HSV-1, HSV-2 or co-infection in a subject. In an embodiment, the virion further comprises an HSV-1 or HSV-2 glycoprotein D on a lipid bilayer thereof. In an embodiment, the HSV-2 glycoprotein D-encoding gene is an HSV-2 $U_S6$ gene.

In an embodiment, of the virus or virion as described, the HSV-1, HSV-2 or co-infection causes a genital ulcer.

An isolated, recombinant herpes simplex virus-2 (HSV-2) is provided having a deletion of an HSV-2 glycoprotein D-encoding gene in the genome thereof.

In an embodiment, the isolated, recombinant HSV-2 further comprises a surface glycoprotein on a lipid bilayer thereof which is a herpes simplex virus-1 (HSV-1) glycoprotein D. In an embodiment, the isolated, recombinant HSV-2 further comprises a non-HSV-2 viral surface glycoprotein on a lipid bilayer thereof. In an embodiment, the isolated, recombinant HSV-2 further comprises a bacterial surface glycoprotein on a lipid bilayer thereof. In an embodiment, the isolated, recombinant HSV-2 further comprises a parasitic surface glycoprotein on a lipid bilayer thereof, wherein the parasite is a parasite of a mammal.

In an embodiment, the HSV-2 glycoprotein D-encoding gene is an HSV-2 US6 gene. In an embodiment, the surface glycoprotein is encoded by a transgene that has been inserted into the genome of the recombinant HSV-2. In an embodiment, the surface glycoprotein is present on a lipid bilayer thereof by way of infecting a cell with a recombinant HSV-2 having a deletion of an HSV-2 glycoprotein D-encoding gene, wherein the cell is or has been transfected to express the surface glycoprotein on a cell membrane thereof, and wherein the recombinant HSV-2 comprising the surface glycoprotein present on a lipid bilayer is produced from the cell. In an embodiment, the viral glycoprotein is from a HIV, an enterovirus, a RSV, an influenza virus, a parainfluenza virus, Pig corona respiratory virus, a rabies virus, a Lassa virus, a bunyavirus, a CMV, or a filovirus. In an embodiment, the glycoprotein is an HIV gp120. In an embodiment, the filovirus is an ebola virus. In an embodiment, the virus is HIV, a *M. tuberculosis*, a *Chlamydia, Mycobacterium ulcerans, M. marinum, M. leprae, M. absenscens, Neisseria gonnorhea*, or a *Treponeme*. In an embodiment, the *Treponeme* is *Treponeme palidum.*

Also provided is a virion of an isolated, recombinant HSV-2 having a deletion of an HSV-2 glycoprotein D-encoding gene in the genome thereof.

In an embodiment, the virion of the isolated, recombinant HSV-2 further comprises a surface glycoprotein on a lipid bilayer thereof which is a herpes simplex virus-1 (HSV-1) glycoprotein D. In an embodiment, the virion of the isolated, recombinant HSV-2 further comprises a non-HSV-2 viral surface glycoprotein on a lipid bilayer thereof. In an embodiment, the virion of the isolated, recombinant HSV-2 further comprises a bacterial surface glycoprotein on a lipid bilayer thereof. In an embodiment, the virion of the isolated, recombinant HSV-2 further comprises a parasitic surface glycoprotein on a lipid bilayer thereof, wherein the parasite is a parasite of a mammal. In an embodiment, the HSV-2 glycoprotein D-encoding gene is an HSV-2 $U_{S6}$ gene. In an embodiment, the surface glycoprotein is encoded by a transgene that has been inserted into the genome of the recombinant HSV-2 of the virion. In an embodiment, the surface glycoprotein is present on a lipid bilayer thereof by way of infecting a cell with a recombinant HSV-2 having a deletion of an HSV-2 glycoprotein D-encoding gene, wherein the cell is or has been transfected to express the surface glycoprotein on a cell membrane thereof, and wherein the recombinant HSV-2 comprising the surface glycoprotein present on a lipid bilayer is produced from the cell. In an embodiment, the virion has been recovered from such. In an embodiment, the viral glycoprotein is from a HIV, an enterovirus, a RSV, an influenza virus, a parainfluenza virus, Pig corona respiratory virus, a rabies virus, a Lassa virus, a bunyavirus, a CMV, or a filovirus. In an embodiment, the glycoprotein is an HIV gp120. In an embodiment, the filovirus is an ebola virus. In an embodiment, the virus is HIV, a *M. tuberculosis*, a *Chlamydia, Mycobacterium ulcerans, M. marinum, M. leprae, M. absenscens, Neisseria gonnorhea*, or a *Treponeme*. In an embodiment, the *Treponeme* is *Treponeme palidum.*

Also provided is an isolated cell comprising therein a virus as described herein or a virion as described herein, wherein the cell is not present in a human being. In an embodiment of the cell, the cell comprises a heterologous nucleic acid encoding a HSV-1 glycoprotein D. In an embodiment of the cell, the cell expresses HSV-1 glycoprotein D on a membrane thereof.

In an embodiment of the cell, the HSV-1 glycoprotein D is encoded by the heterologous nucleic acid, which heterologous nucleic acid is a HSV-1 glycoprotein D gene, or is a nucleic acid having a sequence identical to a HSV-1 glycoprotein D gene.

A vaccine composition comprising a virus as described herein, or a virion as described herein. In an embodiment of the vaccine composition, the vaccine composition comprises an immunological adjuvant.

Also provided is a composition comprising a virus as described herein, or a virion as described herein, wherein the genome of the virus or virion comprises at least a deletion of a second gene, wherein the second gene is necessary for HSV-2 viral replication. In an embodiment, the composition comprises serum from, or is derived from serum from, a mammal into which the virus or virion has been previously introduced so as to elicit an immune response.

Also provided is pharmaceutical composition comprising a virus as described herein, or a virion as described herein, and a pharmaceutically acceptable carrier.

Also provided is a method of eliciting an immune response in a subject comprising administering to the subject an amount of (i) a virus as described herein; (ii) a virion as described herein, (iii) a vaccine as described herein; (iv) a composition as described herein; or (v) a pharmaceutical composition as described herein, in an amount effective to elicit an immune response in a subject.

Also provided is a method of treating an HSV-2 infection in a subject or treating a disease caused by an HSV-2 infection in a subject comprising administering to the subject an amount of (i) a virus as described herein; (ii) a virion as described herein, (iii) a vaccine as described herein; (iv) a composition as described herein; or (v) a pharmaceutical composition as described herein, in an amount effective to treat an HSV-2 infection or treat a disease caused by an HSV-2 infection in a subject.

Also provided is a method of vaccinating a subject for HSV-2 infection comprising administering to the subject an amount of (i) a virus as described herein; (ii) a virion as described herein, (iii) a vaccine as described herein; (iv) a composition as described herein; or (v) a pharmaceutical composition as described herein, in an amount effective to vaccinate a subject for HSV-2.

Also provided is a method of immunizing a subject against HSV-2 infection comprising administering to the subject an amount of (i) a virus as described herein; (ii) a virion as described herein, (iii) a vaccine as described herein; (iv) a composition as described herein; or (v) a pharmaceutical composition as described herein, in an amount effective to immunize a subject against HSV-2.

HSV-2 and HSV-1 diseases are known in the art, and are also described herein. Both treatment and prevention of HSV-2 and HSV-1 diseases are each separately encompassed. Also treatment or prevention of a HSV-2 and HSV-1 co-infection are covered. Prevention is understood to mean amelioration of the extent of development of the relevant disease or infection in a subject treated with the virus, virion, vaccine or compositions described herein, as compared to an untreated subject.

Also provided is a method of producing a virion of a recombinant herpes simplex virus-2 (HSV-2), having a deletion of an HSV-2 glycoprotein D-encoding gene in the genome thereof and comprising an HSV-1 glycoprotein D on a lipid bilayer thereof, comprising infecting a cell comprising a heterologous nucleic acid encoding a HSV-1 glycoprotein D with a recombinant herpes simplex virus-2 (HSV-2) having a deletion of an HSV-2 glycoprotein D-encoding gene in the genome thereof under conditions permitting replication of the recombinant herpes simplex virus-2 (HSV-2) and recovering a recombinant HSV-2 virion comprising an HSV-1 glycoprotein D on a lipid bilayer thereof produced by the cell.

Also provided is a method of producing a virion of a recombinant herpes simplex virus-2 (HSV-2), having a deletion of an HSV-2 glycoprotein D-encoding gene in the genome thereof and comprising a non-HSV-2 surface glycoprotein on a lipid bilayer thereof, comprising infecting a cell comprising a heterologous nucleic acid encoding the non-HSV-2 surface glycoprotein with a recombinant herpes simplex virus-2 (HSV-2) having a deletion of an HSV-2 glycoprotein D-encoding gene in the genome thereof under conditions permitting replication of the recombinant herpes simplex virus-2 (HSV-2) and recovering a recombinant HSV-2 virion comprising a non-HSV-2 surface glycoprotein on a lipid bilayer thereof produced by the cell.

Also provided is a recombinant nucleic acid is provided having the same sequence as a genome of a HSV-2 except that the sequence does not comprise a sequence encoding an HSV-2 glycoprotein D.

Also provided is an isolated, recombinant herpes simplex virus-2 (HSV-2) having a deletion of an HSV-2 glycoprotein D-encoding gene in the genome thereof for treating or preventing an HSV-2 infection in a subject.

Also provided is an isolated, recombinant herpes simplex virus-2 (HSV-2) having a deletion of an HSV-2 glycoprotein D-encoding gene in the genome thereof for treating or preventing an HSV-1 infection in a subject.

Also provided is a virion of an isolated, recombinant HSV-2 having a deletion of an HSV-2 glycoprotein D-encoding gene in the genome thereof for treating or preventing an HSV-2 infection in a subject.

Also provided is a method of treating an HSV-1 infection, or HSV-1 and HSV-2 co-infection, in a subject, or treating a disease caused by an HSV-2 infection or HSV-1 and HSV-2 co-infection in a subject comprising administering to the subject an amount of (i) a virus as described herein; (ii) a virion as described herein, (iii) a vaccine as described herein; (iv) a composition as described herein; or (v) a pharmaceutical composition as described herein, in an amount effective to treat an HSV-2 infection or treat a disease caused by an HSV-2 infection in a subject or an amount effective to treat an HSV-1 and HSV-2 co-infection or treat a disease caused by an HSV-1 and HSV-2 co-infection in a subject.

Also provided is a method of vaccinating a subject for an HSV-1 infection, or HSV-1 and HSV-2 co-infection, comprising administering to the subject an amount of (i) a virus as described herein; (ii) a virion as described herein, (iii) a vaccine as described herein; (iv) a composition as described herein; or (v) a pharmaceutical composition as described herein, in an amount effective to vaccinate a subject for an HSV-1 infection, or HSV-1 and HSV-2 co-infection.

Also provided is a method of immunizing a subject against an HSV-1 infection, or HSV-1 and HSV-2 co-infection, comprising administering to the subject an amount of (i) a virus as described herein; (ii) a virion as described herein, (iii) a vaccine as described herein; (iv) a composition as described herein; or (v) a pharmaceutical composition as described herein, in an amount effective to immunize a subject against an HSV-1 infection, or HSV-1 and HSV-2 co-infection.

In an embodiment of the methods herein for immunizing, vaccinating or eliciting an immune response, passive transfer of the virion or virus or the antibodies or immune factors induced thereby may be effected from one subject to another. The relevant product may be treated after obtention from one subject before administration to a second subject. In a preferred embodiment of the inventions described herein, the subject is a mammalian subject. In an embodiment, the mammalian subject is a human subject.

Also provided is an isolated, recombinant herpes simplex virus-2 (HSV-2) having a deletion of an HSV-2 glycoprotein D-encoding gene in the genome thereof and further comprising a heterogenous antigen of a pathogen. In an embodiment, the heterogenous antigen is a protein, peptide, polypeptide or glycoprotein. In an embodiment, the heterogenous antigen heterogenous antigen with respect to HSV-2, but is an antigen found on or in the relevant "pathogen." Pathogens, viral and bacterial, are described herein. In an embodiment, the pathogen is a bacterial pathogen of a mammal or a viral pathogen of a mammal. In an embodiment, the antigen or the transgene encoding the pathogen is not actually taken or physically removed from the pathogen, but nevertheless has the same sequence as the pathogen antigen or encoding nucleic acid sequence. In an embodiment, the isolated, recombinant HSV-2 comprises a heterogenous antigen of a pathogen on a lipid bilayer thereof. In an embodiment of the isolated, recombinant HSV-2, the pathogen is bacterial or viral. In an embodiment, the pathogen is a parasite of a mammal. In an embodiment, the HSV-2 glycoprotein D-encoding gene is an HSV-2 US6 gene. In an embodiment, the isolated, recombinant HSV-2, the heterogenous antigen is encoded by a transgene that has been inserted into the genome of the recombinant HSV-2.

Also provided is a method of inducing antibody dependent cell mediated cytotoxicity (ADCC) against an antigenic target in a subject comprising administering to the subject an isolated, recombinant herpes simplex virus-2 (HSV-2) having a deletion of an HSV-2 glycoprotein D-encoding gene in the genome thereof and further comprising a heterogenous antigen on a lipid bilayer thereof in an amount effective to induce antibody dependent cell mediated cytotoxicity (ADCC) against an antigenic target.

Recombinant HSV-2 $\Delta gD^{-/+gD-/+}$ expressing the appropriate transgenes will selectively induce antibodies and cellular immune responses that protect against skin or mucosal infections by pathogens.

In an embodiment, the heterogenous antigen is a surface antigen.

In an embodiment, the transgene encodes an antigen from an HIV, a *M. tuberculosis*, a *Chlamydia, Mycobacterium ulcerans, M. marinum, M. leprae, M. absenscens, Neisseria gonnorhea*, or a *Treponeme*. In an embodiment, the *Treponeme* is *Treponeme palidum*. In an embodiment, the transgene is a *M. tuberculosis* biofilm-encoding gene. In an embodiment, the transgene is an HIV gp120-encoding gene.

In an embodiment, the heterogenous antigen is a surface antigen of the antigenic target. In an embodiment, the heterogenous antigen is a parasite antigen. In an embodiment, the heterogenous antigen is a bacterial antigen or a viral antigen.

In an embodiment, the antigenic target is a virus and is a Lassa virus, a human immunodeficiency virus, an RSV, an enterovirus, an influenza virus, a parainfluenza virus, pig corona respiratory virus, a lyssavirus, a bunyavirus, or a Filovirus.

In an embodiment, the antigenic target is a bacteria and is *Mycobaterium tuberculosis, M. ulcerans, M. marinum, M. leprae, M. absenscens, Chlamydia trachomatis, Neisseria gonorrhoeae* or *Treponema pallidum.*

In an embodiment, the isolated, recombinant HSV-2 transgene is a *M. tuberculosis* biofilm-encoding gene or wherein the transgene is an HIV gp120-encoding gene.

In a preferred embodiment of the methods described herein, the subject is a human. In an embodiment of the methods described herein, the subject has not yet been infected with HSV-1, HSV-2 or co-infection. In an embodiment of the methods described herein, the subject has been infected with HSV-1, HSV-2 or co-infection.

As described herein, a co-infection means a co-infection with HSV-1 and HSV-2.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

Herein a genetically engineered deletion mutant of the gD ($U_{S6}$) gene of HSV-2 is disclosed and its safety, immunogenicity, and vaccine efficacy evaluated against intravaginal HSV-2 challenge in the mouse infection model. The gD gene was replaced with a DNA fragment encoding the green fluorescent protein (gfp) and Vero cells expressing HSV-1 gD (VD60 cells) were transfected with this construct and screened for homologous recombinant virus that formed green plaques. Molecular analysis revealed that a precise recombination had been engineered, which replicates in the complementing VD60 cells to high titers but is noninfectious when propagated on non-complementing cells. Intravaginal challenge of wild-type or SCID mice with $10^7$ pfu/mouse of the complemented gD-null virus (designated herein as HSV-2 $\Delta gD^{-/+}$ for the virus that is genotypically gD deleted, but phenotypically complemented by growth on VD60 cells) revealed no virulence, whereas doses as low as $10^4$ pfu/mouse of parental wild-type virus were 100% lethal. Moreover immunization of mice with HSV-2 $\Delta gD^{-/+}$ yielded complete protection against intravaginal challenge with a clinical isolate of HSV-2. Robust humoral and cellular immunity elicited by HSV-2 $\Delta gD^{-/+}$ was measured and it is concluded that gD is required for productive infection in vivo and that an attenuated strain deleted in this essential glycoprotein elicits protective immunity against HSV-2. Thus, HSV-2 $\Delta gD^{-/+}$ is a promising vaccine for prevention or treatment of genital herpes.

Mechanisms and correlates of protection elicited by HSV-2 ΔgD−/+. A gD-2 null virus was generated, and it was demonstrated that it is highly attenuated in both immunocompetent and immunocompromised mice and when tested as a vaccine candidate, induced a protective immune response against intravaginal challenge with HSV-2. Subcutaneous immunizations with HSV-2 ΔgD−/+ will induce humoral and cellular immune responses that are required for protection against intravaginal challenge with both serotypes of HSV (HSV-2 and HSV-1).

HSV-2 ΔgD−/+ initiates an abortive infection: An HSV-2 strain that is deleted for $U_{S6}$ was constructed to assess its contribution in in early signaling events occurring during cell infection [41]. This virus is incapable of infecting host cells, unless it is grown on a gD-complementing cell line (e.g. VD60 cells encoding gD-1 [40, 41]) that encodes $U_{S6}$ under the control of its endogenous promoter (for example, in an embodiment, the gD-1 promoter). Indeed, HSV-2 ΔgD particles isolated from non-complementing cells do not infect epithelial (FIG. 1) or neuronal cells (SK-N-SH, not shown). However, if propagated in VD60 cells a phenotypically complemented virus (ΔgD−/+) is obtained, which is fully capable of infecting cells that are common targets for wild-type HSV-2. However, after infection with ΔgD−/+no infectious particles or viral plaques (pfu) are produced from these cells and the virus fails to spread from infected to uninfected cells, reflecting the requirement for gD in these processes; thus it is an abortive infection.

HSV-2 ΔgD−/+ is safe in the murine infection model: ΔgD−/+ was evaluated for safety in vivo in wild-type and severe combined immunodeficiency (SCID) mice by inoculating high doses subcutaneously or intravaginally. Mice inoculated intravaginally with 10' pfu of ΔgD−/+(titered on complementing cells) did not manifest any signs of virus-induced pathology throughout the experiments, whereas animals inoculated with 1,000-fold less wild-type virus ($10^4$ pfu) succumbed to HSV-2 disease and died starting Day 8 after inoculation (FIG. 2A). Mice inoculated intravaginally with $10^7$ pfu of ΔgD−/+ did not manifest any signs of virus-induced epithelial or neurological disease throughout the experiments (FIGS. 2B and 2C). No infectious virus was recovered from genital tract tissue or DRGs, as determined by plaque assay or co-cultivation of DRGs with Vero cells (not shown).

HSV-2 ΔgD−/+ elicits systemic and mucosal antibodies to HSV-2: Mice inoculated and boosted subcutaneously (sc.-sc.) with ΔgD−/+ or inoculated subcutaneously and boosted intravaginally (sc.-i.vag.) with this candidate vaccine strain ($10^6$ pfu/mouse) elicited a humoral immune response to HSV-2 as evidenced by an increase in serum and vaginal washes anti-HSV-2 antibodies (FIGS. 3A and 3B). The control animals were immunized with an uninfected VD60 cell lysate (referred to as Control). The antibodies were measured by ELISA using infected cell lysates as the antigen (response to uninfected cell lysates subtracted as background). Noteworthy, the magnitude of the antibody response differs depending on the route of immunization. Indeed, s.c.-s.c. immunization elicited significantly more serum and vaginal wash antibodies to HSV-2 than s.c.-i.vag. immunization. This finding suggests that the vaginal wash antibodies likely represent transudate of IgG from the blood and suggest that sc.-sc. is a more appropriate route for eliciting high levels of systemic and local IgG antibodies to HSV-2. Additionally, Mice inoculated and boosted subcutaneously (sc.-sc.) with ΔgD−/+($10^6$ pfu/mouse) elicited a neutralizing anti-HSV-2 as evidenced by in vitro neutralization of Vero cell monolayers with virus and sera from these mice (FIG. 3C).

HSV-2 ΔgD−/+ elicits HSV-2-specific T cell activation: gB498-505-specific transgenic CD8+ T cells (gBT-I) were transferred into C57BL/6 mice prior to vaccination. Vaccinated mice were inoculated with $10^6$ pfu ΔgD−/+ or with VD60 cell lysates (Control). Spleens were harvested on Day 14 after the boost and quantified by flow cytometry using counting beads (CountBright™, Lifetechnologies) (FIG. 4A). At the same day, spleens were stained for memory surface markers and analyzed by flow cytometry (FIG. 4B). Finally, splenocytes harvested the same day were re-stimulated in vitro for 6 hours with the agonist gB498-505-peptide and intracellular cytokine staining was performed to measure IFN-γ production by these cells. Immunization with ΔgD−/+ increased the IFN-γ production in the vaccinated compared to control mice (FIG. 4C). The response in control mice presumably reflects the persistence of the gBT-I T cells in naïve mice after transfer. Similar results were obtained using multiplex cytokine analyses for supernatants of splenocytes re-stimulated in vitro with gB498-505-peptide (not shown). These findings demonstrate that the vaccine induces T cell responses.

Mice immunized with HSV-2 ΔgD−/+ are protected against intravaginal HSV-2 lethal challenge: Animals vaccinated with HSV-2 ΔgD−/+ either sc.-sc. or sc.-i.vag. suffer less body weight after intravaginal lethal dose challenges equivalent to LD90 ($5\times10^4$ pfu/mouse) and survive challenges, whereas mice immunized with the VD60 control lysate succumbed to disease by Day 10 (FIGS. 5A and 5B). The vaccines also provided complete protection against 10 times the LD90 ($5\times10^5$ pfu/mouse, data not shown). This protection was associated with significantly reduced epithelial disease scores (FIG. 5C) and the complete absence of neurological signs (FIG. 5D). Scoring was performed as previously described [44]. Furthermore, significantly less virus was recovered in vaginal washes in ΔgD−/+-immunized mice, as compared to control mice at day 2 post-vaginal challenge suggesting rapid clearance (FIG. 5E). Moreover no infectious virus was recovered in Day 4 vaginal washes (FIG. 5E) or in vaginal tissue or DRGs isolated on Day 5 after challenge (FIG. 5F). The latter suggest that the vaccine prevents virus from reaching and/or replicating in the DRG.

Immunization with HSV-2 ΔgD−/+ prevents inflammation at the infection site after challenge with virulent HSV-2: Mice vaccinated with HSV-2 ΔgD−/+ and intravaginally challenged with virulent HSV-2 display significantly less inflammatory cytokines at the infection site as compared to animals inoculated with VD60 lysates (Control). Indeed, vaccinated mice secreted significantly less TNF-α (FIG. 6A), IL-6 (FIG. 6B) and IL-1(3 (FIG. 6C) in vaginal washes at Day 2 and 7 post-infection than Control mice. Noteworthy, increased levels of inflammatory cytokines are associated with increased HIV replication and shedding at the genitalia in the co-infected with HSV-2 and HIV [45, 46]. A similar phenomenon is also observed in vitro [47].

Immunization with HSV-2 ΔgD−/+ recruits T cells to the infection site and associated LNs. Mice immunized sc.-sc. with ΔgD−/+ displayed increased percentages of activated anti-HSV-2 gBT-I CD8+(FIG. 7A) and CD4+ T cells (FIG. 7B) in sacral lymph nodes (LNs) after challenge with virulent HSV-2. Mice immunized sc.-i.vag. with ΔgD−/+ displayed increased numbers of anti-HSV-2 gBT-I CD8+ (FIG. 7C) and CD4+ T cells (FIG. 7D) in the vagina after challenge with virulent HSV-2 suggesting that vaccination with ΔgD−/+ recruits anti-HSV-2 CD8+ T cells and activated CD4+ T cells (likely anti-HSV-2) to the infection site and associated lymph nodes.

In further experiments, immunization with HSV-2-$\Delta gD^{-i+gD-1}$ was found to confer protection in C57BL/6 and Balb/C to vaginal challenge with virulent HSV-2. In addition, intravaginal HSV-2 challenged $\Delta gD^{-/+gD-1}$ immunized mice had no detectable HSV-2 in vaginal or neural tissue at 5 days post-challenge. HSV-2 ΔgD−/+gD-1 sc.sc. antibodies were found to recognize numerous HSV-2 proteins (both gD and gB) unlike HSV-2 morbid-bound mice. Serum antibodies from vaccinated animals showed neutralization of HSV-1 and HSV-2 in vitro. Moreover, eerum from ΔgD−/+gD-1 vaccinated mice elicited Antibody Dependent Cellular Cytotoxicity (ADCC) of HSV-2 infected cells in vitro.

In summary, HSV-2 ΔgD−/+gD-1 is attenuated and completely safe in wt and SCID mice. Recombinant HSV-2 ΔgD−/+gD-1 protected against lethal HSV-2 intravaginal and HSV-2/HSV-1 skin infection. Protection was observed in two different mouse strains. There was no detectable infection, and sterilizing immunity. Also observed was induction of HSV-2 specific CD8+ T cells and systemic and mucosal HSV Abs. IgG2a and IgG2b were the predominant anti-HSV isotype. Also observed was FcyRIII/II-dependent ADCC. Surprisingly, passive transfer of immune serum protects naïve mice, and FcRn and FcyR knockout mice were not protected with immune sera.

Discussion

The World Health Organization estimated that over 500 million people were infected with herpes simplex virus type 2 (HSV-2) worldwide with approximately 20 million new cases annually [1]. Infection risk increases with age and because the virus establishes latency with frequent subclinical or clinical reactivation, the impact of infection is lifelong. Alarmingly, HSV-2 significantly increases the risk of acquiring and transmitting HIV [2-4]. The prevalence of HSV-2 varies among global regions, fluctuating from 8.4% for Japan up to 70% for sub-Saharan Africa, a region where HIV prevalence is epidemic [5, 6]. In the US the prevalence of HSV-2 is ~16% and that of HSV-1 has declined to ~54%. The decreasing prevalence of HSV-1 in the US (and other European nations) is linked to an increase in genital HSV-1 as evidenced by results in the recent disappointing glycoprotein D (gD) subunit vaccine trial in which the majority of cases of genital herpes disease were caused by HSV-1 [7-9]. While HSV-1 is associated with fewer recurrences and less genital tract viral shedding compared to HSV-2, both serotypes are transmitted perinataly and cause neonatal disease; neonatal disease is associated with high morbidity and mortality even with acyclovir treatment [10-12]. The morbidity associated with genital herpes, its synergy with the HIV epidemic, and its direct medical cost, which surpasses 500 million dollars in the US alone, highlight the imperative to develop a safe and effective vaccine [13].

Subunit formulations consisting of viral envelope glycoproteins combined with adjuvants have predominated the HSV-2 vaccine field for nearly 20 years and the majority of clinical trials have focused on this strategy [8, 14-19]. Although subunit preparations are safe and elicit neutralizing antibodies, these formulations provided little efficacy against HSV-2 infection or disease in clinical trials [8, 14]. Surprisingly, an HSV-2 gD subunit vaccine provided protection against genital HSV-1, but not HSV-2 [8, 20]. Subsequent studies found that serum HSV-2 gD antibody levels correlated with protection against HSV-1, suggesting that the antibody titers required for HSV-2 protection may be higher than those needed to protect against HSV-1 [21]. In contrast, cell mediated immunity (intracellular cytokine responses to overlapping gD peptides) did not correlate with protection against either serotype [21]. The vaccine elicited $CD4^+$, but not $CD8^+$ T cell responses, but there were no differences in $CD4^+$ T cell responses between vaccinated infected and uninfected women [21]. Genital tract or other mucosal antibody responses were not measured. An HSV-2 vaccine candidate with gH deleted from the genome failed to reduce the frequency of viral recurrences in a clinical trial conducted among seropositive subjects, although the vaccine was not evaluated for efficacy against primary infection [29].

Clinical studies showing increased rates of HSV-2 reactivation in HIV-infected patients combined with the failure of the gD subunit vaccine to elicit any $CD8^+$ T cell response despite the induction of neutralizing serum antibodies suggest that an effective vaccine must also elicit protective T cell responses [28, 30-32]. The importance of T cells is further highlighted by studies showing selective retention of HSV-1 reactive T-cells in human trigeminal ganglia. $CD4^+$ and $CD8^+$ T cells were identified surrounding neurons and, while there was heterogenity in the viral proteins targeted, the tegument protein, virion protein 16 (VP16), was recognized by multiple trigeminal ganglia T cells in the context of diverse HLA-A and -B alleles; these findings suggest that tegument proteins may be important immunogens [33]. Similarly, cytotoxic T cells directed at tegument proteins were also identified in studies of humans latently infected with HSV-2 [34]. $CD8^+$ T cells (including $CD8\alpha\alpha^+$ T cells) persist in genital skin and mucosa at the dermal-epidermal junction following HSV reactivation suggesting that they play a role in immune control [35].

Herein is disclosed an engineered an HSV-2 virus genetically deleted for native HSV-2 gD. The HSV-2 gD gene encodes an envelope glycoprotein essential for viral entry and cell-to-cell spread. Glycoprotein D also binds to tumor necrosis factor receptor superfamily member 14 (TNFRSF14), an immune-regulatory switch also known as herpesvirus entry mediator (HVEM). Because HVEM harbors docking sites for more than one ligand and signaling differs depending on whether these molecules bind to HVEM in cis or in trans, gD may have modulatory effects on immune cells [36, 37]. Indeed, recent studies suggest that gD competes with the natural ligands for this receptor and modulates the cytokine response to the virus [38, 39]. The gD gene was replaced with a DNA fragment encoding the green fluorescent protein (gfp) and transformed complementing Vero cells expressing HSV-1 gD (VD60 cells [40]) (e.g. gD-1 under gD-1 promoter) with this construct were screened for homologous recombinant virus that formed green plaques. The mutant virus replicates in the complementing Vero cell line to high titers (designated HSV-2 $\Delta gD^{-/+}$ when passaged on complementing cells), but is noninfectious in non-complementing cells (designated HSV-2 $\Delta gD^{-/-}$ when isolated from non-complementing cells). This virus was purified and characterized in vitro [41]. Intravaginal or subcutaneous inoculation of immunocompetent or immunocompromised (SCID) mice revealed no virulence compared to the lethal infection caused by parental wild-type virus. Immunization (subcutaneous prime followed by a single boost administered either subcutaneously or intravaginally) was 100% protective against intravaginal challenge with virulent HSV-2. Robust humoral and cellular immunity was elicited by HSV-2 $\Delta gD^{-/+}$ and it was concluded that $U_S6$ (gD-2) is required for productive infection in vivo. This live attenuated viral strain will provide sterilizing immunity against HSV. Also passive serum or serum product transfer can be employed.

Example 2

The ability of the vaccine to protect against clinical HSV-1 and HSV-2 isolates was further confirmed, as was the local immune response at the site of infection. Classically, HSV primarily infects genital or oral nucleated epidermal cells due to breaches in the skin or mucocutaneous layers in humans (75). To more closely model human HSV infection, a skin scarification model was used for these studies, which displays viral kinetics and histopathology similar to humans (76).

Results

Figures 8A, 8B, 8C:
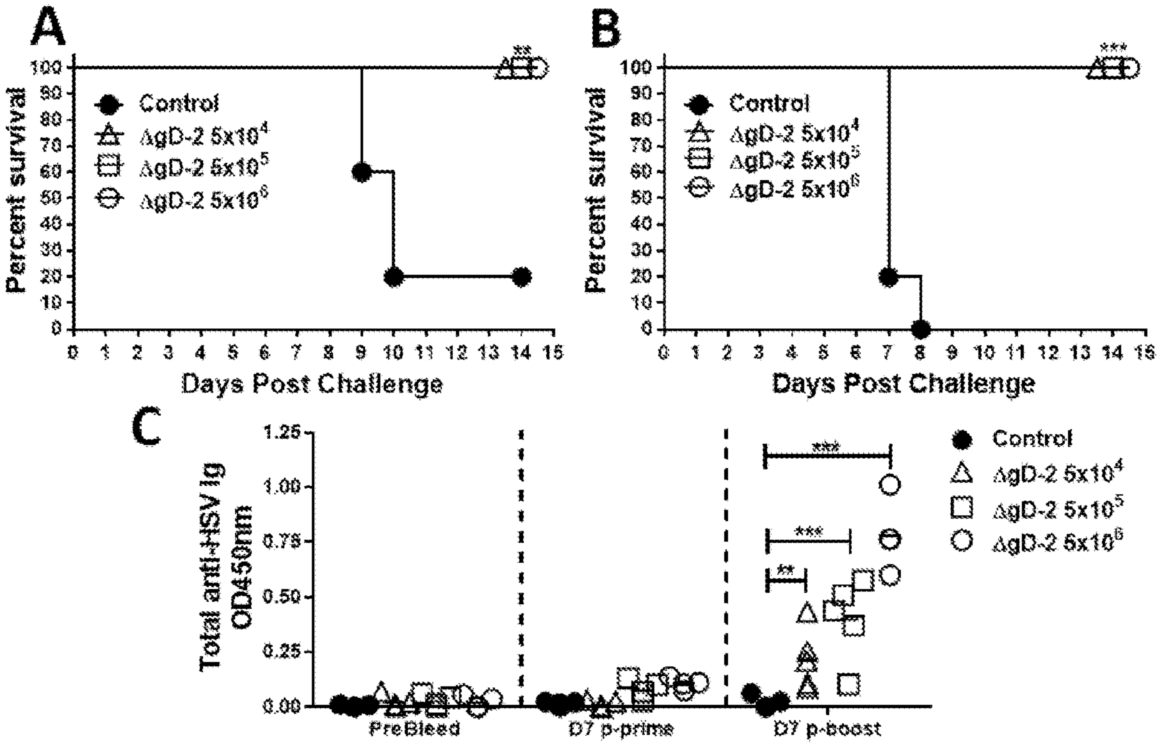
FIG. 8A-8C. HSV-2 ΔgD-2 provides complete protection against disease following intravaginal or skin challenge with vaccine doses as low as $5\times10^4$ PFU. C57BL/6 mice were primed and then 21 days later boosted subcutaneously (sc) with either $5\times10^4$ PFU, $5\times10^5$ PFU, $5\times10^6$ PFU of HSV-2ΔgD-2 or VD60 lysates (control). Mice were subsequently challenged 21 days after boost with an LD90 of HSV-2 (4674) either (8A) intravaginally or (8B) via skin scarification and followed for survival (n=5 mice/group) and disease scores. (8C) Serum was assessed for HSV-2 antibodies before (PreBleed), day 7 post-prime, and day 7 post boost via ELISA (line represents mean). *p<0.05, p<0.01, *p<0.001, ΔgD-2 vaccinated groups vs. control-vaccinated group via two-way ANOVA. Kaplan Meier analysis was used for survival curves.

Immunization with low doses of ΔgD-2 are protective against lethal intravaginal and skin challenges. Previous studies were conducted with $5\times10^6$ PFU (titer determined on complementing VD60 cells) of ΔgD-2 as the vaccine inoculum. A dose de-escalation study was conducted to determine protection at lower doses of vaccination. C57BL/6 mice (5 mice/group) were subcutaneously (sc) primed and boosted 21 days later with $5\times10^6$ PFU, $5\times10^5$ PFU, or $5\times10^4$ PFU of ΔgD-2. Three weeks later the mice were challenged either intravaginally or by skin scarification with an $LD_{90}$ ($5\times10^5$ PFU) of HSV-2(4674), a previously described clinical isolate (77). All HSV-2 ΔgD-2 immunized mice survived (5/5 per group), whereas all of the control-vaccinated mice (immunized with VD60 cell lysate) succumbed to disease (FIG. 8A, 8B). Although the mice vaccinated with the lowest dose ($5\times10^4$) showed mild epithelial disease, no signs of neurological disease were observed and all animals completely recovered by day 14 in both the vaginal and skin challenge models. HSV antibodies (measured by ELISA) were detected in the serum of all vaccinated mice one week after boost, but not prime, and the antibody titer increased with administration of higher vaccine doses (FIG. 8C).

Mice immunized with ΔgD-2 are protected from high viral challenges of virulent HSV-1 and HSV-2 clinical isolates. To evaluate if the ΔgD-2 vaccine protects against diverse HSV-1 and HSV-2 strains, five HSV-1 were obtained (denoted B3x1.1-B3x1.5) and five HSV-2 (denoted B3x2.1-B3x2.5) clinical isolates from the Clinical Virology Lab at Montefiore located in the Bronx, N.Y. as well as a South African HSV-2 clinical isolate ($SD_{90}$). The isolates were grown on Vero cells and were passaged no more than three times before sequencing and phenotyping. Illumina sequencing showed that the strains exhibited substantial genetic diversity with pairwise distances as high as 6.3% between B3x1.5 and the other B3x1 isolates and 5.0% between B3x2.2 and the other B3x2 isolates. In vivo virulence of each clinical strain was compared to laboratory strains by challenging Balb/C mice using the skin scarification model with $1\times10^5$ PFU of the HSV-1 strains or $5\times10^4$ PFU of HSV-2 strains. The clinical isolates demonstrated a range of virulence with B3x1.1, B3x1.3, B3x2.3, and SD % inducing more rapid disease with the highest morbidity in naïve mice. Similar results were observed in the vaginal challenge model with the same 4 isolates exhibiting the most virulent disease (not shown). Interestingly, no differences between the isolates were observed by in vitro single and multistep growth curves on Vero cells.

Figures 9A, 9B, 9C, 9D:
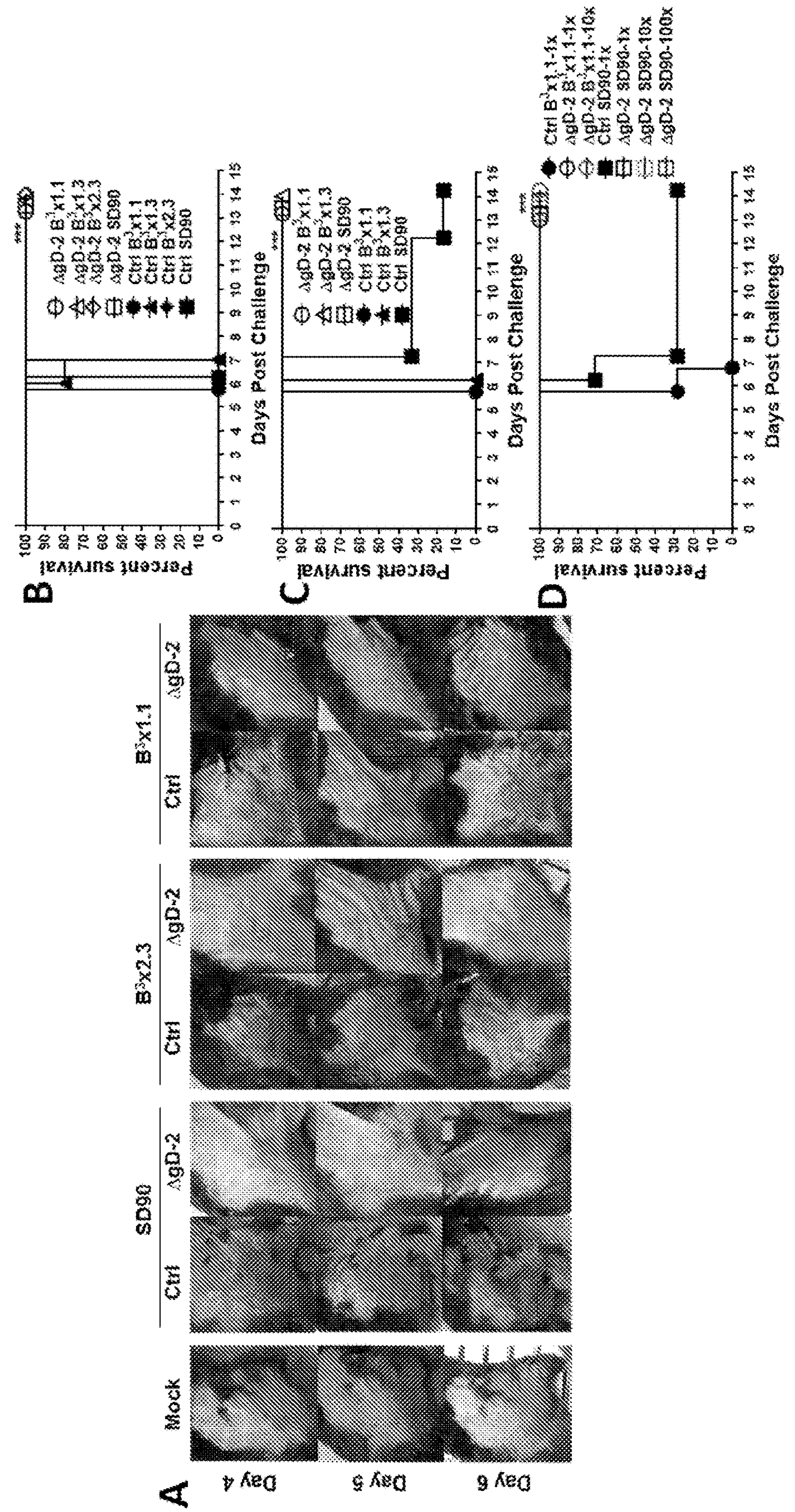
FIG. 9A-9D. Mice vaccinated with HSV-2 ΔgD-2 are protected against clinical isolates of HSV-1 and HSV-2. C57BL/6 (n=7 mice/group) or Balb/C (n=5 mice/group) mice were immunized with ΔgD-2 or VD60 cell lysates (Control) and subsequently challenged with an LD90 dose of most virulent isolates and monitored daily for lesions in the skin (9A; representative images from C57BL/6 mice), survival (9B; C57BL/6 mice and 9C; Balb/C) Additional C57BL/6 mice were challenged with 10 and 100 times (10× and 100×) the LD90 dose of SD90 and 10× the LD90 of $Bx^3$1.1 and monitored for survival (9D). Survival for HSV-2 ΔgD-2-vaccinated group vs. control-vaccinated group were compared by Kaplan Meier analysis, ***p<0.001).

To assess if ΔgD-2 protected against the different isolates, C57BL/6 or Balb/C mice were primed and boosted with $5\times10^6$ PFU/mouse of ΔgD-2 (or VD60 lysate as the control immunogen) and then challenged with an LD90 dose of the 4 more virulent clinical isolates (Table 1) using the skin scarification model. All ΔgD-2 vaccinated mice survived challenge (n=7 C57BL/6 mice per group; FIG. 3A, and n=5 Balb/C mice per group, FIG. 9B). While some mice exhibited mild epithelial disease, which peaked on Day 4, the majority of animals had fully recovered by day 8 post-challenge. No signs of neurological disease were detected in any of the mice at any time point.

TABLE 1

HSV strains used in vaccine efficacy studies

| Viral Strain | Origin of Isolate | HSV Serotype | Lethal $Dose_{90}$* |
|---|---|---|---|
| $B^3 \times 1.1$ | United States | Type 1 | $5 \times 10^5$ pfu |
| $B^3 \times 1.3$ | United States | Type 1 | $1 \times 10^5$ pfu |
| SD90 | South Africa | Type 2 | $5 \times 10^4$ pfu |
| $B^3 \times 2.3$ | United States | Type 2 | $1 \times 10^5$ pfu |
| 4674 | United States | Type 2 | $5 \times 10^5$ pfu |

Figures 10A, 10B, 10C, 10D:
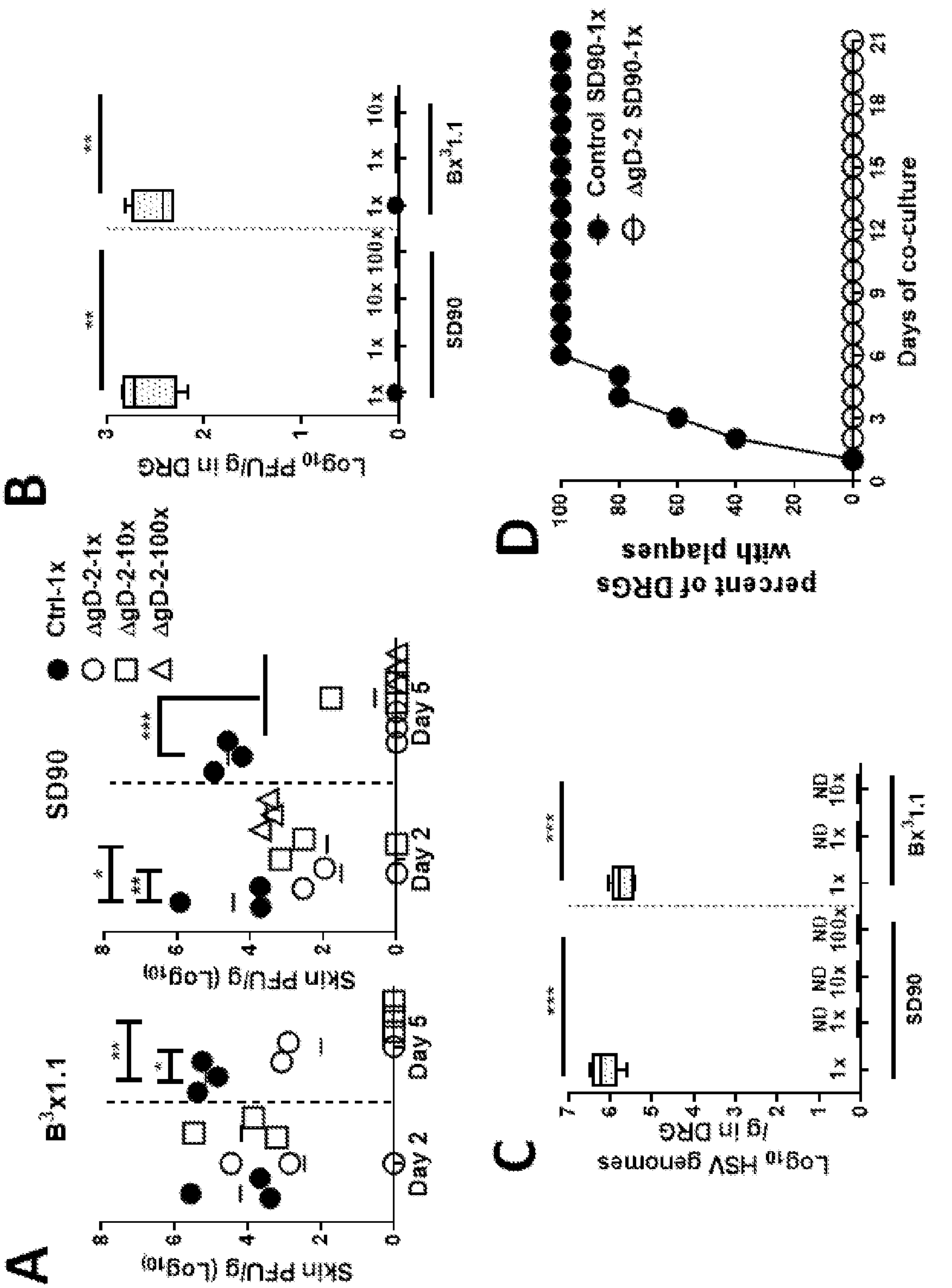
FIG. 10A-10D. Virus is rapidly cleared and no latent virus is detected in HSV-2 ΔgD-2 immunized mice following challenge with clinical isolates. Mice were immunized with ΔgD-2 or VD60 cell lysates (Control) and subsequently challenged by skin scarification with an 1× or 10× the LD90 of HSV-1($B^3$x1.1) or with 1×, 10× or 100× the LD90 of HSV-2(SD90) (n=5 mice per group). Skin biopsies were obtained on day 2 and day 5 post-challenge and assayed for viral load by plaque assay on Vero cells (10A) (n=3 samples/group, line represents mean). The presence of replicating or latent HSV in DRG tissue obtained from ΔgD-2 vaccinated (day 14 post challenge) or control vaccinated (time of euthanasia) mice by plaque assay (10B) and qRT-PCR (10C), respectively (n=5 mice/group). Latency was further evaluated by co-culturing Vero cells with DRG isolated from ΔgD-2 and control immunized mice that were challenged with an LD90 of HSV-2 SD90 at day 5 post-challenge (10D). Data in Panels B and C are presented as box and whisker plots with black dots indicating outliers. HSV-2 ΔgD-2-vaccinated group and control-vaccinated groups were compared by student's t-test; *p<0.05; p<0.01; *p<0.001.

Note: *Plaque forming units that cause 90% morbidity in Balb/C mice skin challenge model To further evaluate the robustness of the immune response, the challenge dose was increased in the C57BL/6 mice to 10× and 100× the $LD_{90}$ doses of SD90 and 10× the $LD_{90}$ of B3x1.1. All of the ΔgD-2 vaccinated mice survived (FIG. 9D) with no signs of neurological disease. The ΔgD-2 vaccinated mice had significantly reduced virus detected in skin biopsies by day 5 post-challenge with the majority having no viral plaques detected (FIG. 10A, n=3 mice per group). Consistent with the rapid clearance of virus, histopathology of skin biopsies revealed ulceration and necrosis covering 75-95% of the epithelium in control-vaccinated mice compared to <10% epithelial necrosis and ulceration in both the ΔgD-2 vaccinated mice and mock (unvaccinated, uninfected) treated mice. Moreover, there was no replicating or latent virus detected by plaque assay (FIG. 10B) or qPCR (FIG. 10C), respectively, in DRGs isolated on Day 14 post-challenge in the ΔgD-2 vaccinated mice (n=5 mice per each challenge dose and strain). Similarly, reactivating virus was not detected when DRGs from ΔgD-2 vaccinated mice (isolated Day 5 post-challenge with LD90 of SD90) were co-cultured for 3 weeks with Vero cells. In contrast, viral DNA and reactivatable virus was recovered from all control (VD60 cell lysate)-vaccinated mice (DRG isolated at time of euthanasia) (FIG. 10D, n=5 mice per group).

Figures 11A, 11B, 11C, 11D:
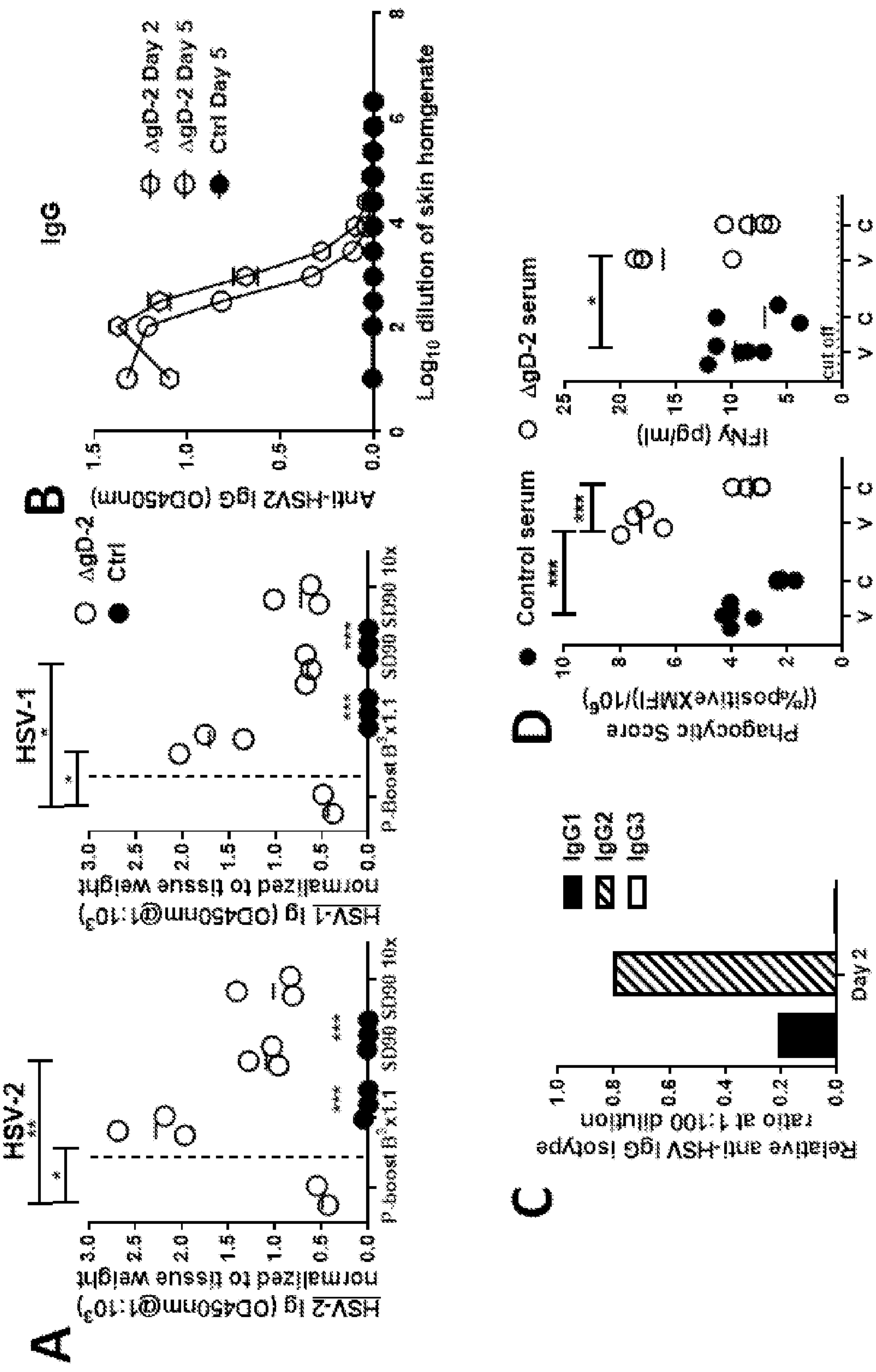
FIG. 11A-11D. HSV-2 IgG2 specific antibodies are rapidly recruited into the skin of HSV-2 ΔgD-2 vaccinated mice following viral challenge. (11A) Mice were immunized with ΔgD-2 or VD60 cell lysates (Control) and subsequently challenged with HSV-1($B^3$x1.1) and HSV-2(SD90) clinical isolates on the skin. Skin biopsies were obtained 21 days post-boost and day 2 post-challenge and evaluated for the presence of anti-HSV antibodies in homogenates (1:$10^3$ dilution) by ELISA using an HSV-2 (left) or HSV-1 (right) infected cell lysate as the antigen (n=3 mice per group, line represents mean). To further quantify the HSV-specific antibodies in the skin, pools of skin homogenates were serially diluted and assayed in the HSV-2 ELISA (6 mice per pool and results are mean±SD obtained from duplicates) (11B). The ratio of anti-HSV-2 IgG sub-isotypes in the day 2 post-challenge skin homogenate pool was determined using sub-isotype specific secondary antibodies (11C). Antibody-dependent-cellular-phagocytosis (ADCP) activity (left panel) of serum from HSV-2 ΔgD-2 or control vaccinated mice 7 days post-boost was quantified using THP-1 monocytic cell line and beads coated with HSV-2 viral cellular lysates (v) or cellular lysates (c). IFN-γ levels (right panel) were measured in the supernatants 8 hr post THP-1 and Ab/bead incubation (11D). The % ADCP is calculated as percent of cells positive for beads multiplied by the MFI of positive cells divided by $10^6$ (left panel). (*p<0.05; p<0.01; *p<0.001, HSV-2 ΔgD-2 vs. control-vaccinated group, student's t-test)

HSV-2 ΔgD-2 recruits HSV-2 specific IgG2 antibodies and immune cells into the skin following challenge: To characterize the immune response to the vaccine and viral challenge in the skin, biopsies were obtained 21 days post boost and 2 or 5 days-post challenge and processed for histology and/or homogenized and then evaluated for presence of HSV-specific Abs by ELISA using either an HSV-2(4674) or HSV-1(17) infected cell lysate as the antigen. The ΔgD-2 immunized mice had low levels of HSV-specific Abs detected in the skin post-boost, which rapidly increased as early as day 2 post-challenge (FIG. 11A). B3x1.1 elicited higher titer Ab response compared to SD90. As expected, no HSV-specific Abs were detected in the skin of control-vaccinated mice on Day 2 or Day 5 post-challenge (FIGS. 11A and 11B). The Abs recovered from the skin were predominantly IgG [1:24,000 titer, (FIG. 11B)] with no detectable anti-HSV IgA or IgM (data not shown), and were enriched in IgG2 (equal induction of IgG2a and IgG2b) HSV specific antibodies (~80% of all HSV IgG) (FIG. 11C).

Murine IgG2 antibodies bind FcγR (78). The Abs elicited by the ΔgD-2 vaccine mediated ADCC and the studies were extended by measuring antibody-dependent-cellular-phagocytosis (ADCP) against HSV coated beads. Serum from ΔgD-2 vaccinated mice obtained 1 week post-boost elicited higher HSV specific phagocytosis and induced greater IFN-γ secretion compared to serum from control immunized mice or beads coated with cell lysates (FIG. 11D).

Figures 12A, 12B, 12C, 12D, 12E, 12F, 12G, 12H:
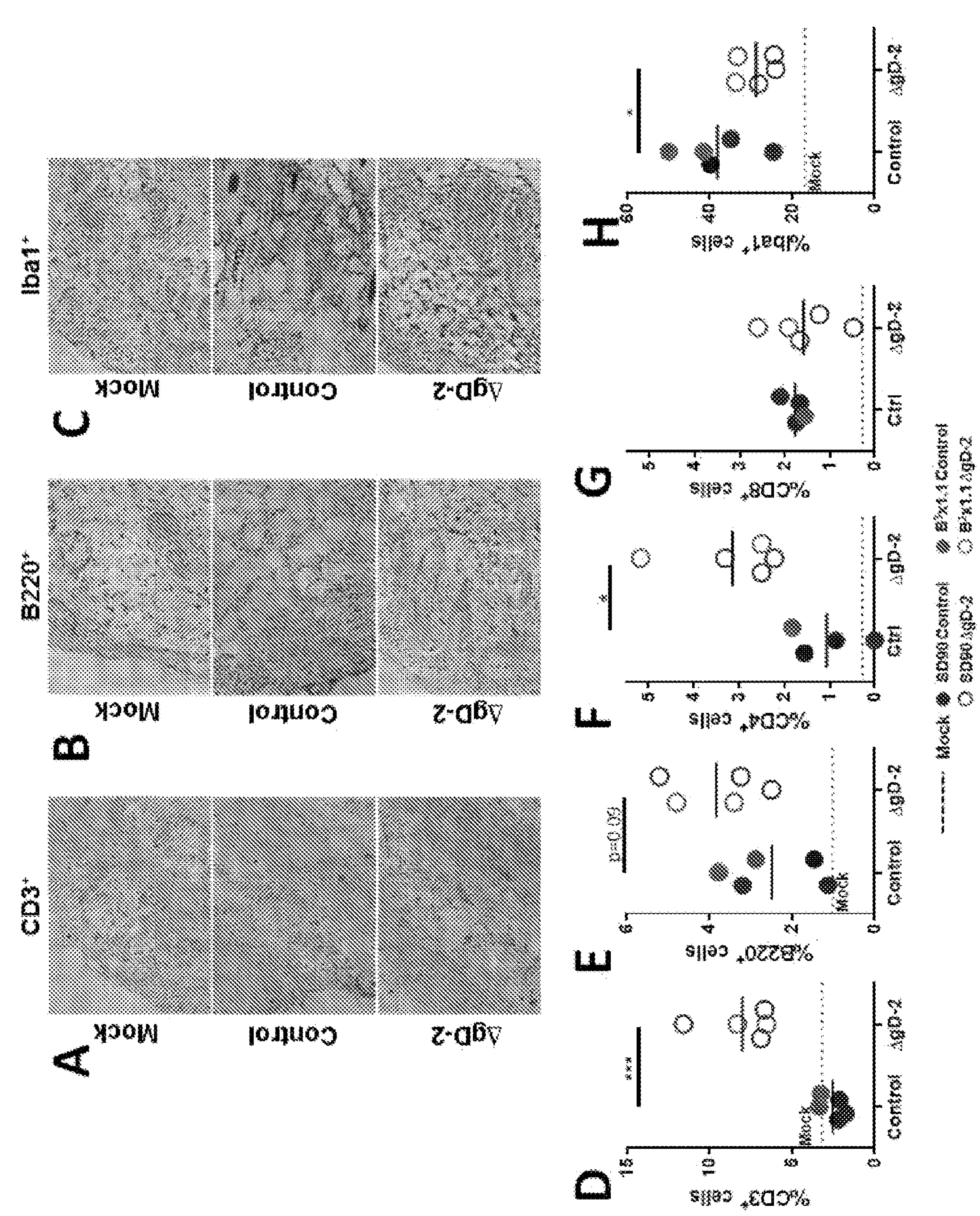
FIG. 12A-12H. Adaptive and innate immune cells are recruited to infected skin by day 5 post-challenge in HSV-2 ΔgD-2 vaccinated mice. Skin sections from mice immunized with ΔgD-2 or VD60 lysates (control) and then challenged with LD90 of SD90 or $Bx^3$1.1 or unvaccinated mock-infected controls were stained for $CD3^+$ (T cells) (12A), $B220^+$ (B cells) (12B) or $Iba1^+$ (pan macrophage) (12C); representative immunohistochemistry images following challenge with HSV-1($B^3$x1.1) or HSV-2(SD90) are shown. The percentage of $CD3^+$ (12D), $B220^+$ (12E), and $Iba1^+$ (12F) cells were enumerated by counting 3 random fields per mouse (5 mice per group). Skin sections were also stained for $CD4^+$ (12G) and $CD8^+$ (12H) by immunofluorescence and the percentage positive cells quantified. Each symbol is the average of the 2 fields for individual mouse and the line represents mean; the dashed line represents counts from unvaccinated, mock-infected mice (3 fields averaging for 1 mouse) (*p<0.05, ΔgD-2-vs. control-vaccinated group by student's t-test).
Figure 13:
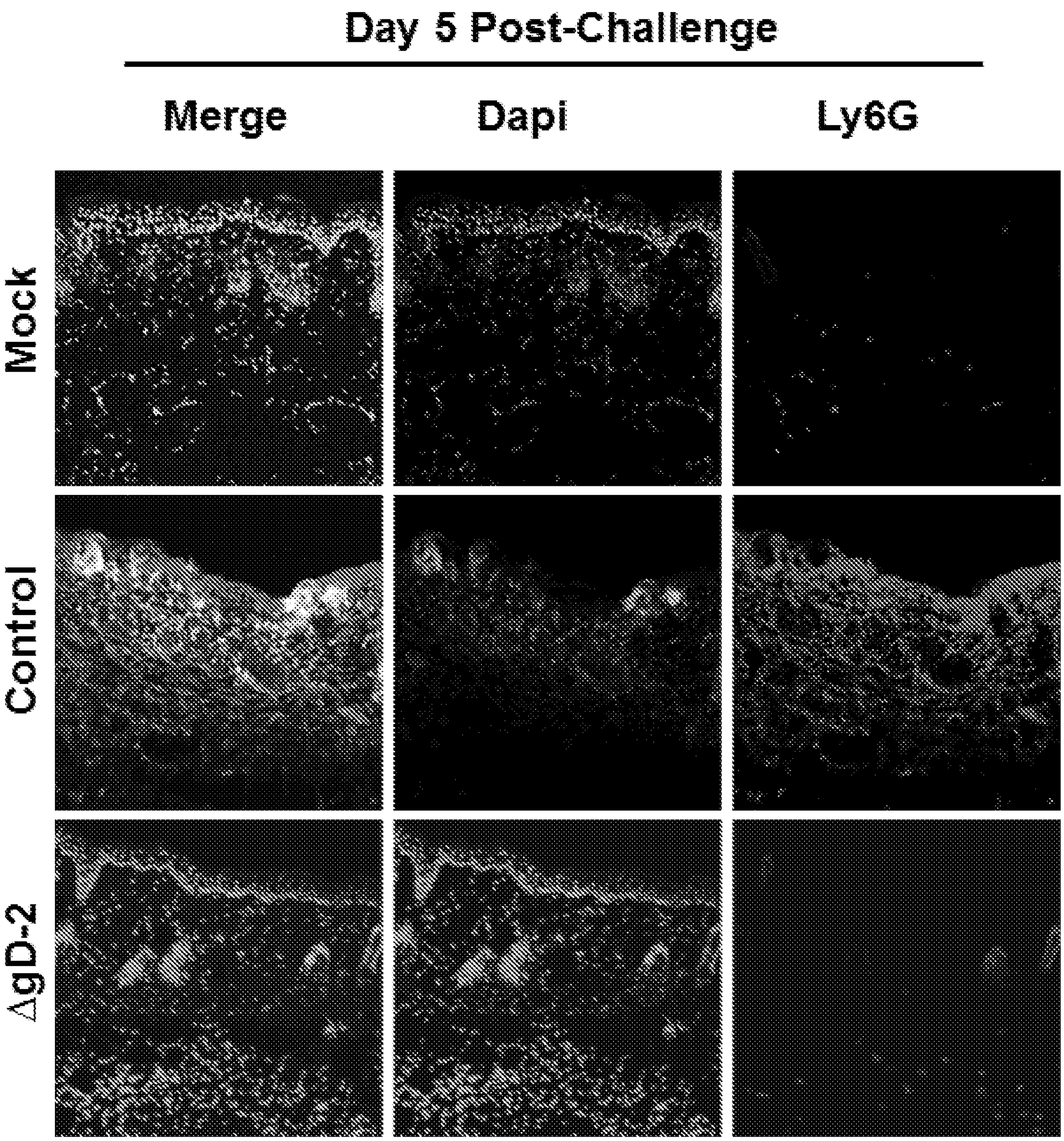
FIG. 13. Control but not ΔgD-2 vaccinated mice have persistent neutrophil infiltration in skin biopsies. Skin sections of unimmunized mock-infected mice or mice immunized with HSV-2 ΔgD-2 or VD60 lysates (control) and infected with HSV-1($B^3$x1.1) virus were harvested on Day 5 post-challenge and stained for neutrophils using Ly6G (red). Nuclei are stained blue with DAPI.

Skin biopsies from ΔgD-2-immunized and control vaccinated mice obtained on Day 5 post-challenge or unimmunized, uninfected mice (mock) were also evaluated by immunohistochemistry and/or immunofluorescence for immune cell responses. The ΔgD-2-immunized mice have a marked increase in CD3+ T cells (mean±SD 8.0%±2.1 vs. 2.5%±0.7, p<0.001; FIGS. 12A, 12D) and B220+ B cells (3.8%+1.1 vs; 2.4%±1.1, p=0.09; FIG. 12B, 12E) compared to control immunized mice. The T-cells were further characterized by staining for CD4 or CD8; there was a significant increase in the CD4+ population but not the CD8+ population in ΔgD-2 compared to control-immunized mice (p<0.05) (FIGS. 12F and 12G). Conversely, there was a decrease in Iba1+ monocyte/macrophage cells (FIGS. 12C and 12H) and Ly6G+ neutrophils (FIG. 13) in ΔgD-2 compared to control immunized mice.

Figures 14A, 14B, 14C, 14D, 14E, 14F:
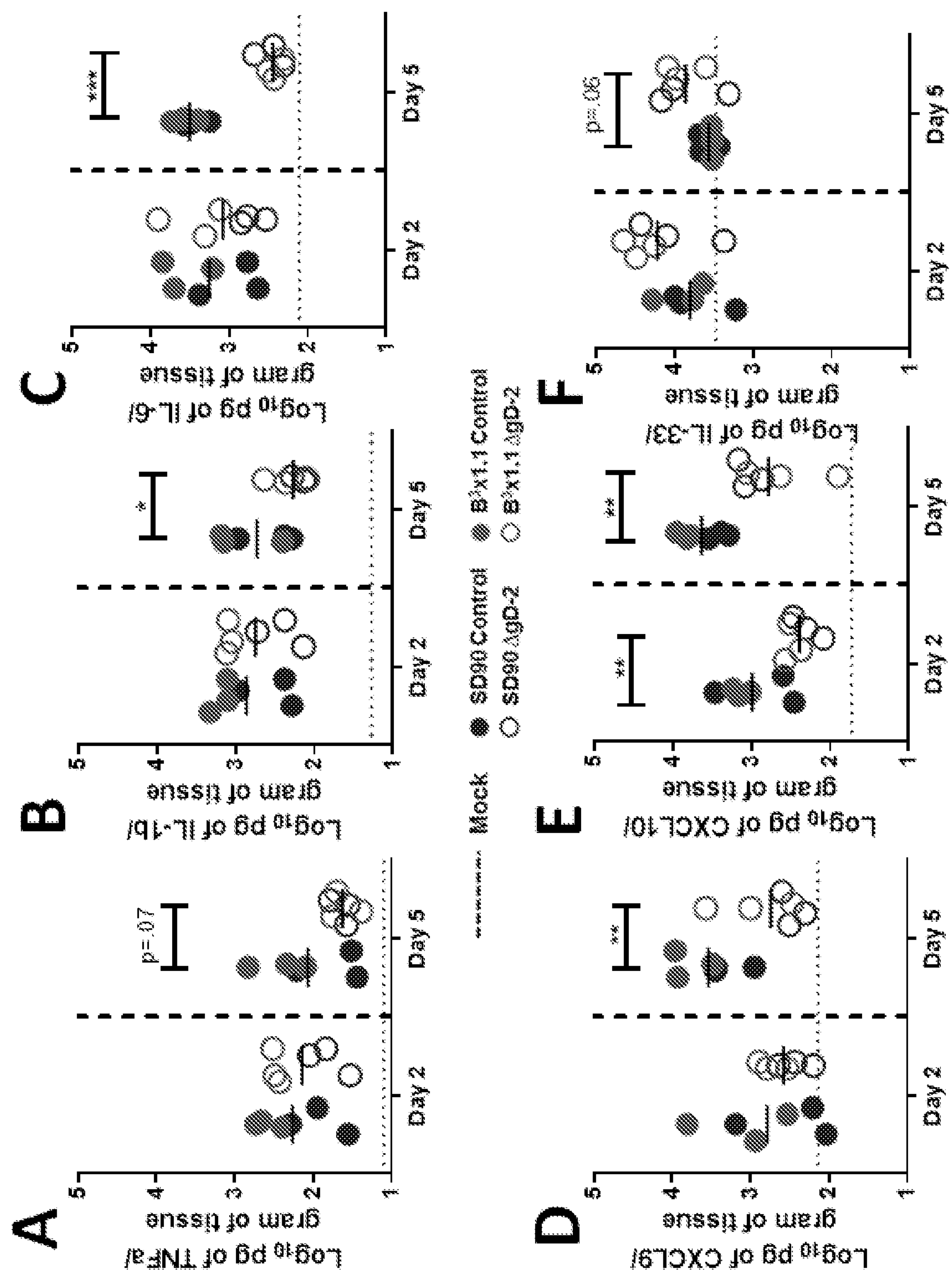
FIG. 14A-14F. Mice immunized with ΔgD-2 have decreased inflammatory cytokines and chemokines in the skin compared to control immunized mice by day 5 post-challenge. Biopsies of skin from mice immunized with ΔgD-2 or VD60 lysates (Control) at day 2 or day 5 post-challenge (or unimmunized, uninfected controls) were homogenized and evaluated for TNF (14A), IL-1β (14B), IL-6 (14C), CXCL9 (14D), CXCL10 (IP-10) (14E), and IL-33 (14F) (n=6 animals/group, line represents mean, dashed line represents counts from unimmunized, mock infected animals). (*p<0.05; p<0.01; *p<0.001, HSV-2 ΔgD-2-vaccinated group vs. control-vaccinated group students t-test.

Consistent with the decrease in inflammatory cells and rapid clearance of virus, there was a decrease in inflammatory cytokines/chemokines detected in skin homogenates in the ΔgD-2 compared to control immunized mice on Day 5 post-challenge (FIG. 14). HSV-1 and HSV-2-infected mice had higher levels of TNFα (FIG. 14A), IL-1(3 (FIG. 14B), and IL-6 (FIG. 14C) compared to mock-infected mice on Day 2 independent of immunization. However, the levels decreased by Day 5 in ΔgD-2 but not the control-immunized mice. Similar results were obtained for the chemokines CXCL9 (FIG. 14D) and CXCL10 (FIG. 14E). Interestingly, IL-33 levels were consistently higher in ΔgD-2-immunized compared to control-immunized mice at both time points (FIG. 14F).

Discussion

This study further confirms that vaccination with HSV-2 ΔgD-2 affords complete protection against a panel of genetically diverse HSV-1 and HSV-2 clinical isolates and prevents the establishment of latency. Vaccine efficacy was confirmed in an optimized skin model, which is reflective of human primary disease. The ΔgD-2 elicited high titer antibodies that were rapidly recruited into the skin resulting in clearance of virus by day 5 even following challenge with 100-times the LD90 of the most virulent strain, SD90. The protective effect of ΔgD-2 against a broad array of HSV-1 and HSV-2 clinical isolates differentiates it from other candidate vaccines such as HSV-2 ΔUL5/ΔUL29, which failed to fully protect against the clinical isolate SD90, or gD subunit vaccines and others that have only been tested against one or two laboratory viral strains.

The broad protection afforded by ΔgD-2 likely reflects the unique nature of the immune response elicited. The Abs induced were enriched for the IgG2 subtype (~80% of all HSV-specific IgG), had low level neutralizing activity (not shown), were rapidly recruited into the skin with titers reaching 1:24,000 in skin biopsies by day 2 post-challenge, and mediated Fc effector functions (78) including ADCP (shown here) and ADCC. The antibody response to ΔgD-2 was dose-dependent, correlated with the rapidity of viral clearance as evidenced by disease scores and likely contributed to the vaccine's ability to completely prevent the establishment of latency. Although immunization with lower doses of ΔgD-2 elicited a lower titer of HSV-specific antibody in the serum, all of the mice were protected from lethal challenge. These findings suggest that lower levels of antibody may be sufficient for FcγR-effector functions. A different HSV-2 viral strain in which the nectin-1 binding domain of gD is altered (gD27), also elicited lower titers of serum neutralizing Abs compared to recombinant adjuvanted gD, but, conversely, was more protective than recombinant gD protein against vaginal challenge in mice (59). Other antibody functions such as ADCC or ADCP were not evaluated. However, these findings further support the notion that neutralizing Ab titers are not a predictive correlate of protection in mice, cotton rats (80), or humans.

While a rapid inflammatory response characterized by increases in cytokines and chemokines was observed in both control vaccinated and ΔgD-2 vaccinated mice on Day 2 post-challenge, the inflammatory response resolved in the vaccinated mice by Day 5, which is consistent with the rapid clearance of virus. In contrast, inflammation persisted in the control vaccinated mice, consistent with progressive disease. The latter was characterized by persistently elevated cytokines/chemokines (IL-1β, IL6, CXCL9 and CXCL10) and the persistence of monocytes/macrophages and neutrophils, which were observed throughout the epithelium and within the dermal layer in the control-vaccinated mice. In contrast, a higher percentage of CD4+ T cells and B220+ B cells were observed in the skin of ΔgD-2 vaccinated mice on Day 5, presumably reflecting a cellular memory response.

Interestingly, IL-33 was the only cytokine that trended higher in the skin from the ΔgD-2 immunized mice compared to controls. The precise role of IL-33 is not known. Prior studies have shown that rIL-33 administration enhanced skin wound healing in mice and was associated with activation of innate lymphoid cells and differentiation of monocytes into type 2 macrophages (81, 82). Systemic administration of IL-33 to mice was associated with an increase in FcgR2b, which is linked to decreased inflammation (88). Possibly, the increase in IL-33 observed in the skin of ΔgD-2 vaccinated mice promoted wound healing and resolution of inflammation.

The clinical isolates displayed variable virulence in the murine skin (and vaginal) model despite similar in vitro growth kinetics (76, 84). Interestingly, however, although a similar level of genetic diversity was seen among HSV-1 isolates to that described in previous studies, substantially greater genetic diversity was found among the HSV-2 isolates collected in the Bronx than those described in previous reports. The greater differences observed here may reflect the diverse geographic origins of the Bronx community. Despite this heterogeneity, all of the isolates tested were completely protected by ΔgD-2 vaccine, possibly reflecting the polyantigenic response. Moreover, complete protection was observed against both HSV-1 and HSV-2, which is clinically relevant, as HSV-1 has emerged as the more common cause of genital disease in the developed world. The universal protection observed here combined with the "sterilizing immunity" as evidenced by absence of latent virus supports the effectiveness of this ΔgD-2 vaccine.

Material and Methods

Cells and viruses: Vero (African green monkey kidney cell line; CCL-81; American Type Culture Collection (ATCC), Manassas, Va., USA) cells, VD60 cells [Vero cells encoding gD-1 under endogenous promoter (85)], and CaSki (human cervical epithelial cell line; CRL-1550; ATCC) were passaged in DMEM supplemented with 10% fetal bovine serum (FBS, Gemini Bio-Products, West Sacramento, Calif.). THP-1 (human monocyte cell line; TIB-202; ATCC) cells were passaged in RPMI-1640 (Life Technologies) supplemented with 10% FBS and sub-cultured according to ATCC guidelines. Construction of HSV-2(G) ΔgD-2 and its propogation on VD60 cells has been previously described (95, 94). No variability in vaccine efficacy has been observed comparing 5 different viral preparations. HSV-2 (4674) (86) was propagated on CaSki cells. Laboratory strains HSV-2(G) (87), HSV-2 (333-ZAG) (86), HSV-1(17) (89), and HSV-1(F) (87) were propagated on Vero cells. South African isolate HSV-2(SD90) (97) was provided by David Knipe and propagated on Vero cells. Five HSV-1 (B3x1.1 through B3x1.5) and five HSV-2 (B3x2.1 through B3x2.5) de-identified clinical isolates were provided by the Clinical Virology Lab at Montefiore and passaged three times on Vero cells for a low-passage working stock.

In vitro growth curves: Single-step and multi-step growth curves were performed as previously described (86). For single-step growth of each virus, Vero cells were infected with virus at a multiplicity of infection (moi) of 5 PFU/cell and supernatants and cells were collected every 4, 8, 16 and 24 hours (h) post-infection (pi) and stored at −80° C. For multi-step growth of each virus, Vero cells were infected at a moi of 0.01 PFU/cell and supernatants and cells were harvested every 12 h pi up to 72 hours. Infectious virus was measured by performing plaque assays with supernatants and lysed cells.

Viral DNA isolation and sequencing of clinical isolates: HSV DNA was prepared by infecting confluent Vero cells in a T150 flask with each of the B3x clinical isolates at an MOI of 10. Cells were harvested 16 hpi and washed twice with PBS. DNA was extracted using DNeasy® Blood and Tissue (Qiagen) following the manufacturer's recommendations. DNA was quantitated by Qubit dsDNA hs assay (Life Technologies). Paired-end libraries were prepared by the Nextera XT DNA library preparation kit (Illumina) following the manufacturer's instructions. Libraries were sequenced on a Illumina MiSeq Desktop Sequencer. Viral genome sequences were assembled with the VirAmp pipeline (89) following removal of host sequence by alignment to the *Macaca mulatta* genome as a substitute for the incomplete *Chlorocebus sabaeus* (source of Vero cells) genome. HSV-1 and HSV-2 genomes were annotated with Genome Annotation Transfer Utility on ViPR by comparison to HSV-1(96) (GenBank accession no. JN555585.1) & HSV- 2(HG52) (JN561323) prior to submission to GenBank. Whole genome alignments including the previously sequenced HSV-2(SD90e) (KF781518), HSV-2(333) (KP192856), ChHV 105640 (NC_023677.1), & HSV-1(F) (GU734771.1) were performed using ClustalW (90) and phylogenetic trees were constructed using the UPGMA method with 1000 bootstrap replicates in MEGA6 (91). All positions containing gaps or missing data were eliminated. GenBank numbers for the genome sequences are as follows: HSV-2(G) (KU310668), HSV-2(4674) (KU310667), B3x1.1 (KU310657), B3x1.2 (KU310658), B3x1.3 (KU310659), B3x1.4 (KU310660), B3x1.5 (KU310661), B3x2.1 (KU310662), B3x2.2 (KU310663), B3x2.3 (KU310664), B3x2.4 (KU310665), B3x2.5 (KU310666).

Murine immunization and viral challenge studies: Experiments were performed with approval from Albert Einstein College of Medicine Institutional Animal Care and Use Committee, Protocol #20130913 and #20150805. Female C57BL/6 and BALB/c mice were purchased from Jackson Laboratory (JAX, Bar Harbor, Me.) at 4-6 weeks of age. Mice were primed and boosted 3 weeks later with $5\times10^4$-$5\times10^6$ PFU of ΔgD-2 or equal amount of VD60 cell lysates (Control) subcutaneously (sc, medial to the hind limb and pelvis) at 100 μl/mouse. The titer was determined by a plaque assay on complementing cells (VD60).

For intravaginal HSV infections, mice were treated with 2.5 mg of medoxyprogesterone acetate (MPA; Sicor Pharmaceuticals, Irvine, Calif.) sc five days prior to challenge. Mice were then inoculated intravaginally with an LD90 (5×10^5 pfu/mouse) of HSV-2(4674) at 30 μl/mouse and scored for disease and monitored for survival for 14 days as previously described (21). For HSV skin infections, mice were depilated on the right flank with Nair and allowed to rest for 24 hr. Depilated mice were anesthetized with isoflurane (Isothesia, Henry-Schein), then abraded on the exposed skin with a disposable memory board for 20-25 strokes and subsequently challenged with $1\times10^5$ PFU HSV-1 or $5\times10^4$ PFU HSV-2 strains for in vivo virulence studies or challenged with an $LD_{90}$, $10\times LD_{90}$, or $100\times LD_{90}$ of select HSV strains (see Table 1) for vaccine efficacy studies. Mice were monitored for 14 days and scored as follows: 1: primary lesion or erythema, 2: distant site zosteriform lesions, mild edema/erythema, 3: severe ulceration and edema, increased epidermal spread, 4: hind-limp paresis/paralysis and 5: death. Mice that were euthanized at a score of 4 were assigned a value of 5 on all subsequent days for statistical analyses.

HSV RT-qPCR: DNA was extracted from weighed tissue samples using DNeasy® Blood and Tissue (Qiagen) following the manufacturer's recommendations. Extracted DNA was then normalized to 10 ng of DNA per reaction and viral DNA quantified using real-time quantitative PCR (RT-qPCR, qPCR) using ABsolute qPCR ROX Mix (Thermo Scientific). Primers for HSV polymerase (UL30) were purchased from Integrated DNA Technologies (Cat #: 1179200494) and used to detect viral genomic DNA. Isolated HSV-2 viral DNA was calibrated for absolute copy amounts using QuantStudio® 3D Digital PCR (dPCR, ThermoFisher Scientific) and subsequently used as a standard curve to determine HSV viral genome copies. Samples that read 4 or less copy numbers were considered negative. Data are presented as log 10 HSV genomes per gram of DRG (dorsal root ganglia) tissue.

Detection of antibodies and cytokines in skin biopsies: Skin biopsies were obtained from HSV-2 ΔgD-2 or VD60 lysates (control) immunized mice (~5-10 mm in diameter by mechanical excision) day 21 post-boost or day 2 and 5 post viral skin challenge. The tissue was weighed and homogenized in RNase/DNase free Lysing Matrix A tubes (MP Biomedicals, Santa Ana, Calif.) with serum-free DMEM at 6.0 m/sec for three 30 sec cycles in the FastPrep-24™ 5G (MP Biomedicals). Samples were spun at 5000 rpm for 10 min at 4° C. and the resulting supernatant was evaluated for anti-HSV antibodies, cytokines and chemokines. Anti-HSV antibodies were detected by ELISA as previously described using uninfected, HSV-1(96), or HSV-2(4674)-infected Vero cell lysates as the coating antigen (94). Biotin anti-mouse Ig κ or biotin anti-mouse IgA, IgM, IgG1, IgG2a, IgG2b, or IgG3 at 1 μg/ml (Becton Dickenson, San Diego) were used as secondary detection antibodies. Wells were read on a SpectraMax (M5 series) ELISA plate reader at an absorbance of 450 nm. The resulting absorbance was determined by subtracting values obtained for uninfected cell lysates to values obtained with infected cell lysates. Total anti-HSV Ig is reported as the optical density (OD) at 450 nm normalized to relative tissue weight at a 1:1000 dilution of tissue homogenate. Anti-HSV IgG, IgA, IgM, or IgG1-3 are reported as the optical density (OD) at 450 nm at all dilutions except IgG1-3 which is reported only at a 1:100 dilution of skin homogenate.

Skin homogenate supernatants were assayed for interleukin-6 (IL-6), IL-1 beta (IL-1β), IL-33, tumor necrosis factor alpha (TNFα), monokine induced by interferon-gamma (MIG, CXCL9), interferon-inducible cytokine (IP-10, CXCL10) using a Milliplex mouse cytokine/chemokine immunoassay (Millipore, Danvers, Mass.) and a Luminex Magpix system and analyzed with Milliplex Analyst (Version 3.5.5.0; VigeneTech Inc.).

Histopathology, immunohistochemistry and immunofluorescence of skin tissue: Mice were euthanized on Day 5 post-challenge and the skin at the viral (or mock) infection site was excised and formalin fixed for 48 hrs at RT. Samples were processed routinely to be paraffin-embedded and sectioned. Slides for histopathology were stained with hematoxylin and eosin (H&E). Samples were evaluated histologically by a board certified veterinary pathologist which were blinded of samples identity. For immunohistochemistry (IHC), the samples were sectioned to 5 μm, deparaffinized in xylene followed by graded alcohols. Antigen retrieval was performed in 10 mM sodium citrate buffer at pH 6.0, heated to 96° C., for 30 minutes. Endogenous peroxidase activity was blocked using 3% hydrogen peroxide in water. The sections were stained by routine IHC methods, using Super-PicTure™ (ThermoFisher Scientific, Cat:87-9673) against rabbit primary antibodies to anti-CD3 (Ready to use format, ThermoFisher Scientific, Cat: RM-9107-R7), anti-B220 (BD Biosciences Cat: 550286), or anti-Iba1 (1:3000 dilution Wako Pure Chemical Industries, Richmond, Va.) and then stained with diaminobenzidine as the final chromogen. All immunostained sections were lightly counterstained with hematoxylin. Stained cross-sections were photomicrographed with Zeiss Axio Observer inverted light microscope at 20× magnification from apical layer (epidermal) to basal layer (striated muscle) at 3 different locations per sample. Stained-positive cells were enumerated as described by Bologna-Molina et al., 2011 (92). Data is represented as the average of % positive cells=(positive nucleated cells/total nucleated cells) of three photomicrographed sections per sample.

For Immunofluorescent studies, skin tissue was excised 5 days post-HSV or mock skin challenge and then frozen in OCT media. Samples were cut into 5 μm sections and stored at −80° C. Frozen slides were then fixed in −20° C. acetone for 15 mins, washed with wash buffer (WB, 0.05% Tween 20 in PBS), then blocked for 2 hrs with blocking buffer (2% BSA, 5% heat inactivated goat serum in PBS) at RT. Slides were washed twice and incubated with anti-CD4(GK1.5, 1:200), anti-CD8 (YTS169.4, 1:250), anti-Ly6G (1A8, 1:500) in blocking buffer for 1 hr at RT. Slides were thoroughly washed and incubated with an goat anti-rat secondary antibody conjugated with either Alexa flour 555 or Alexa flour 488 (1:500 or 1:200, respectively) for 30 min at RT. Slides were washed and mounted with media containing DAPI (ProLong® Diamond Antifade Mountant with DAPI, ThermoFisher Scientific). Slides were imaged using a Nikon Eclipse Ti-U inverted light microscope at 20× magnification from apical layer (epidermal) to basal layer (striated muscle) at two different locations per sample. For % CD4+ and % CD8+ quantification, total nucleated cells were calculated by DAPI positive objects ≥5 μm via a software algorithm from Velocity (version 6.3, PerkinElmer). CD4 or CD8 positive cells were counted manually for fluorescence and incorporation of a DAPI+ nuclei to exclude non-specific staining of hair follicles and cellular debris in the skin sections. Data is represented as the average of % positive cells=(positive cells/total DAPI cells) of two images per sample.

Antibody dependent cellular phagocytosis (ADCP) assay. To determine HSV specific ADCP, a protocol modified from Ackerman et al., 2011 (93) was used. Briefly, 2×108 1 μm Neutravadin-red fluorescent beads (Invitrogen, F-8775) were coated with 0.3 mg of biotinylated HSV-2 infected or uninfected (control) Vero cells overnight at 4° C. in 500 μl of BlockAid™ (ThermoFisher Scientific, B-10710). Beads were washed twice with 1% BSA in PBS and then $1\times10^6$ beads/well were added in a 96 round bottom plate. Serum from immunized mice at 1 week post boost was heat-inactivated at 56° C. for 30 min and diluted 1:5 in serum-free RPMI. 50 μl of diluted serum was added to wells that contained the HSV lysates or control cell lysates coated beads and incubated for 2 h at 37° C. $2\times10^4$ cells/well THP-1 cells were added to each at a final volume of 200 μl/well and incubated for 8 hr at 37° C. at 5% $CO_2$. Subsequently, 100 μl of supernatant was removed and stored at −20° C. then resuspended with 100 μl 4% paraformaldehyde. Samples were then read on 5-laser LSRII flow cytometer (Becton Dickenson, San Diego) at the Einstein Flow Cytometry Core Facility. Phagocytic score is reported by gating on events representing THP-1 cells then applying the following equation: [(% of cells bead positive X MFI of cells positive for beads)/$10^6$] using FlowJo software (version 10, Tree Star Inc.). IFN-γ secretion from activated THP-1 cells via antibody phagocytosis was determined by analyzing stored cultured supernatants using a Milliplex human custom immunoassay (Millipore, Danvers, Mass.) and a Luminex Magpix system as previously described.

Virus detection in tissue. Skin and dorsal root ganglia (DRG) were weighed and homogenized as described above. Supernatants of homogenized tissue were then overlaid on confluent Vero cell monolayers (2×105 cells/well in a 48-well plate) for 1 h. Wells were washed with PBS and then with 199 medium (Gibco®) containing 1% heat-inactivated FBS, overlaid with 0.5% methylcellulose and incubated at 37° C. for 48 h. Cells were fixed with 2% paraformaldehyde, stained with a crystal violet solution and the number of PFU quantified. Neuronal ex-vivo co-culture assays were performed as previously described (94).

Statistical analysis. Results were compared by two-way analysis of variance (2-way ANOVA) with multiple comparisons or unpaired student's t-tests using GraphPad Prism version 6 (San Diego, Calif.). Mantel-Cox survival curves were compared by log rank tests. P values <0.05 (*), <0.01 (), <0.001 (*) were considered significant.

REFERENCES

1. Looker, K. J., G. P. Garnett, and G. P. Schmid, An estimate of the global prevalence and incidence of herpes simplex virus type 2 infection. Bull World Health Organ, 2008. 86(10): p. 805-12, A.
2. Freeman, E. E., et al., Herpes simplex virus 2 infection increases HIV acquisition in men and women: systematic review and meta-analysis of longitudinal studies. AIDS, 2006. 20(1): p. 73-83.
3. Gray, R. H., et al., Probability of HIV-1 transmission per coital act in monogamous, heterosexual, HIV-1-discordant couples in Rakai, Uganda. Lancet, 2001. 357(9263): p. 1149-53.
4. Wald, A. and K. Link, Risk of human immunodeficiency virus infection in herpes simplex virus type 2-seropositive persons: a meta-analysis. J Infect Dis, 2002. 185(1): p. 45-52.
5. Paz-Bailey, G., et al., Herpes simplex virus type 2: epidemiology and management options in developing countries. Sex Transm Infect, 2007. 83(1): p. 16-22.
6. Doi, Y., et al., Seroprevalence of herpes simplex virus 1 and 2 in a population-based cohort in Japan. J Epidemiol, 2009. 19(2): p. 56-62.
7. Bradley, H., et al., Seroprevalence of herpes simplex virus types 1 and 2—United States, 1999-2010. J Infect Dis, 2014. 209(3): p. 325-33.
8. Belshe, R. B., et al., Efficacy results of a trial of a herpes simplex vaccine. N Engl J Med, 2012. 366(1): p. 34-43.
9. Bernstein, D. I., et al., Epidemiology, clinical presentation, and antibody response to primary infection with herpes simplex virus type 1 and type 2 in young women. Clin Infect Dis, 2013. 56(3): p. 344-51.
10. Kimberlin, D., Herpes simplex virus, meningitis and encephalitis in neonates. Herpes, 2004. 11 Suppl 2: p. 65A-76A.
11. Ward, K. N., et al., Herpes simplex serious neurological disease in young children: incidence and long-term outcome. Arch Dis Child, 2012. 97(2): p. 162-5.
12. Lafferty, W. E., et al., Recurrences after oral and genital herpes simplex virus infection. Influence of site of infection and viral type. N Engl J Med, 1987. 316(23): p. 1444-9.
13. Owusu-Edusei, K., Jr., et al., The estimated direct medical cost of selected sexually transmitted infections in the United States, 2008. Sex Transm Dis, 2013. 40(3): p. 197-201.
14. Mertz, G. J., et al., Double-blind, placebo-controlled trial of a herpes simplex virus type 2 glycoprotein vaccine in persons at high risk for genital herpes infection. J Infect Dis, 1990. 161(4): p. 653-60.
15. Group, H. S. V. S., et al., Safety and immunogenicity of a glycoprotein D genital herpes vaccine in healthy girls 10-17 years of age: results from a randomised, controlled, double-blind trial. Vaccine, 2013. 31(51): p. 6136-43.
16. Leroux-Roels, G., et al., Immunogenicity and safety of different formulations of an adjuvanted glycoprotein D genital herpes vaccine in healthy adults: a double-blind randomized trial. Hum Vaccin Immunother, 2013. 9(6): p. 1254-62.
17. Bernstein, D. I., et al., Safety and immunogenicity of glycoprotein D-adjuvant genital herpes vaccine. Clin Infect Dis, 2005. 40(9): p. 1271-81.

18. Stanberry, L. R., et al., Glycoprotein-D-adjuvant vaccine to prevent genital herpes. N Engl J Med, 2002. 347(21): p. 1652-61.
19. Corey, L., et al., Recombinant glycoprotein vaccine for the prevention of genital HSV-2 infection: two randomized controlled trials. Chiron HSV Vaccine Study Group. JAMA, 1999. 282(4): p. 331-40.
20. jh.richardus@rotterdam.nl, Safety and immunogenicity of a glycoprotein D genital herpes vaccine in healthy girls 10-17 years of age: Results from a randomised, controlled, double-blind trial. Vaccine, 2013. 31(51): p. 6136-43.
21. Belshe, R. B., et al., Correlate of Immune Protection Against HSV-1 Genital Disease in Vaccinated Women. J Infect Dis, 2013.
22. Gerber, S. I., B. J. Belval, and B. C. Herold, Differences in the role of glycoprotein C of HSV-1 and HSV-2 in viral binding may contribute to serotype differences in cell tropism. Virology, 1995. 214(1): p. 29-39.
23. Lubinski, J. M., et al., The herpes simplex virus 1 IgG fc receptor blocks antibody-mediated complement activation and antibody-dependent cellular cytotoxicity in vivo. J Virol, 2011. 85(7): p. 3239-49.
24. Para, M. F., L. Goldstein, and P. G. Spear, Similarities and differences in the Fc-binding glycoprotein (gE) of herpes simplex virus types 1 and 2 and tentative mapping of the viral gene for this glycoprotein. J Virol, 1982. 41(1): p. 137-44.
25. Hook, L. M., et al., Herpes simplex virus type 1 and 2 glycoprotein C prevents complement-mediated neutralization induced by natural immunoglobulin M antibody. J Virol, 2006. 80(8): p. 4038-46.
26. Lubinski, J. M., et al., Herpes simplex virus type 1 evades the effects of antibody and complement in vivo. J Virol, 2002. 76(18): p. 9232-41.
27. Awasthi, S., et al., Immunization with a vaccine combining herpes simplex virus 2 (HSV-2) glycoprotein C (gC) and gD subunits improves the protection of dorsal root ganglia in mice and reduces the frequency of recurrent vaginal shedding of HSV-2 DNA in guinea pigs compared to immunization with gD alone. J Virol, 2011. 85(20): p. 10472-86.
28. Manservigi, R., et al., Immunotherapeutic activity of a recombinant combined gB-gD-gE vaccine against recurrent HSV-2 infections in a guinea pig model. Vaccine, 2005. 23(7): p. 865-72.
29. de Bruyn, G., et al., A randomized controlled trial of a replication defective (gH deletion) herpes simplex virus vaccine for the treatment of recurrent genital herpes among immunocompetent subjects. Vaccine, 2006. 24(7): p. 914-20.
30. Ouwendijk, W. J., et al., T-cell immunity to human alphaherpesviruses. Curr Opin Virol, 2013. 3(4): p. 452-60.
31. Parr, M. B. and E. L. Parr, Mucosal immunity to herpes simplex virus type 2 infection in the mouse vagina is impaired by in vivo depletion of T lymphocytes. J Virol, 1998. 72(4): p. 2677-85.
32. Noisakran, S. and D. J. Carr, Lymphocytes delay kinetics of HSV-1 reactivation from in vitro explants of latent infected trigeminal ganglia. J Neuroimmunol, 1999. 95(1-2): p. 126-35.
33. van Velzen, M., et al., Local CD4 and CD8 T-cell reactivity to HSV-1 antigens documents broad viral protein expression and immune competence in latently infected human trigeminal ganglia. PLoS Pathog, 2013. 9(8): p. e1003547.
34. Muller, W. J., et al., Herpes simplex virus type 2 tegument proteins contain subdominant T-cell epitopes detectable in BALB/c mice after DNA immunization and infection. J Gen Virol, 2009. 90(Pt 5): p. 1153-63.
35. Zhu, J., et al., Immune surveillance by CD8alphaalpha+ skin-resident T cells in human herpes virus infection. Nature, 2013. 497(7450): p. 494-7.
36. Steinberg, M. W., et al., Regulating the mucosal immune system: the contrasting roles of LIGHT, HVEM, and their various partners. Semin Immunopathol, 2009. 31(2): p. 207-21.
37. Steinberg, M. W., T. C. Cheung, and C. F. Ware, The signaling networks of the herpesvirus entry mediator (TNFRSF14) in immune regulation. Immunol Rev, 2011. 244(1): p. 169-87.
38. Kopp, S. J., C. S. Storti, and W. J. Muller, Herpes simplex virus-2 glycoprotein interaction with HVEM influences virus-specific recall cellular responses at the mucosa. Clin Dev Immunol, 2012. 2012: p. 284104.
39. Yoon, M., et al., Functional interaction between herpes simplex virus type 2 gD and HVEM transiently dampens local chemokine production after murine mucosal infection. PLoS One, 2011. 6(1): p. e16122.
40. Ligas, M. W. and D. C. Johnson, A herpes simplex virus mutant in which glycoprotein D sequences are replaced by beta-galactosidase sequences binds to but is unable to penetrate into cells. J Virol, 1988. 62(5): p. 1486-94.
41. Cheshenko, N., et al., HSV activates Akt to trigger calcium release and promote viral entry: novel candidate target for treatment and suppression. FASEB J, 2013. 27(7): p. 2584-99.
42. Parr, E. L. and M. B. Parr, Immunoglobulin G is the main protective antibody in mouse vaginal secretions after vaginal immunization with attenuated herpes simplex virus type 2. J Virol, 1997. 71(11): p. 8109-15.
43. Mbopi-Keou, F. X., et al., Cervicovaginal neutralizing antibodies to herpes simplex virus (HSV) in women seropositive for HSV Types 1 and 2. Clin Diagn Lab Immunol, 2003. 10(3): p. 388-93.
44. Hendrickson, B. A., et al., Decreased vaginal disease in J-chain-deficient mice following herpes simplex type 2 genital infection. Virology, 2000. 271(1): p. 155-62.
45. Nixon, B., et al., Genital Herpes Simplex Virus Type 2 Infection in Humanized HIV-Transgenic Mice Triggers HIV Shedding and Is Associated With Greater Neurological Disease. J Infect Dis, 2013.
46. Carr, D. J. and L. Tomanek, Herpes simplex virus and the chemokines that mediate the inflammation. Curr Top Microbiol Immunol, 2006. 303: p. 47-65.
47. Stefanidou, M., et al., Herpes simplex virus 2 (HSV-2) prevents dendritic cell maturation, induces apoptosis, and triggers release of proinflammatory cytokines: potential links to HSV-HIV synergy. J Virol, 2013. 87(3): p. 1443-53.
48. Bourne, N., et al., Herpes simplex virus (HSV) type 2 glycoprotein D subunit vaccines and protection against genital HSV-1 or HSV-2 disease in guinea pigs. J Infect Dis, 2003. 187(4): p. 542-9.
49. Bourne, N., et al., Impact of immunization with glycoprotein D2/AS04 on herpes simplex virus type 2 shedding into the genital tract in guinea pigs that become infected. J Infect Dis, 2005. 192(12): p. 2117-23.
50. Bernstein, D. I., et al., The adjuvant CLDC increases protection of a herpes simplex type 2 glycoprotein D vaccine in guinea pigs. Vaccine, 2010. 28(21): p. 3748-53.

51. Bernstein, D. I., et al., Potent adjuvant activity of cationic liposome-DNA complexes for genital herpes vaccines. Clin Vaccine Immunol, 2009. 16(5): p. 699-705.

52. Sweeney, K. A., et al., A recombinant *Mycobacterium smegmatis* induces potent bactericidal immunity against *Mycobacterium tuberculosis*. Nat Med, 2011. 17(10): p. 1261-8.

53. Kohl, S., et al., Limited antibody-dependent cellular cytotoxicity antibody response induced by a herpes simplex virus type 2 subunit vaccine. J Infect Dis, 2000. 181(1): p. 335-9.

54. John, M., et al., Cervicovaginal secretions contribute to innate resistance to herpes simplex virus infection. J Infect Dis, 2005. 192(10): p. 1731-40.

55. Nugent, C. T., et al., Analysis of the cytolytic T-lymphocyte response to herpes simplex virus type 1 glycoprotein B during primary and secondary infection. J Virol, 1994. 68(11): p. 7644-8.

56. Mueller, S. N., et al., Characterization of two TCR transgenic mouse lines specific for herpes simplex virus. Immunol Cell Biol, 2002. 80(2): p. 156-63.

57. Wallace, M. E., et al., The cytotoxic T-cell response to herpes simplex virus type 1 infection of C57BL/6 mice is almost entirely directed against a single immunodominant determinant. J Virol, 1999. 73(9): p. 7619-26.

58. Milligan, G. N., et al., T-cell-mediated mechanisms involved in resolution of genital herpes simplex virus type 2 (HSV-2) infection of mice. J Reprod Immunol, 2004. 61(2): p. 115-27.

59. Wang, K., et al., A herpes simplex virus 2 glycoprotein D mutant generated by bacterial artificial chromosome mutagenesis is severely impaired for infecting neuronal cells and infects only Vero cells expressing exogenous HVEM. J Virol, 2012. 86(23): p. 12891-902.

60. Barletta, R. G., et al., Identification of expression signals of the mycobacteriophages Bxb1, L1 and TM4 using the *Escherichia-Mycobacterium* shuttle plasmids pYUB75 and pYUB76 designed to create translational fusions to the lacZ gene. J Gen Microbiol, 1992. 138(1): p. 23-30.

61. Yamaguchi, S., et al., A method for producing transgenic cells using a multi-integrase system on a human artificial chromosome vector. PLoS One, 2011. 6(2): p. e17267.

62. Xu, Z., et al., Accuracy and efficiency define Bxb1 integrase as the best of fifteen candidate serine recombinases for the integration of DNA into the human genome. BMC Biotechnol, 2013. 13: p. 87.

63. Hill, A., et al., Herpes simplex virus turns off the TAP to evade host immunity. Nature, 1995. 375(6530): p. 411-5.

64. Shu, M., et al., Selective degradation of mRNAs by the HSV host shutoff RNase is regulated by the UL47 tegument protein. Proc Natl Acad Sci USA, 2013. 110(18): p. E1669-75.

65. Umbach, J. L., et al., MicroRNAs expressed by herpes simplex virus 1 during latent infection regulate viral mRNAs. Nature, 2008. 454(7205): p. 780-3.

66. Cheshenko, N., et al., Herpes simplex virus triggers activation of calcium-signaling pathways. J Cell Biol, 2003. 163(2): p. 283-93.

67. Cheshenko, N. and B. C. Herold, Glycoprotein B plays a predominant role in mediating herpes simplex virus type 2 attachment and is required for entry and cell-to-cell spread. J Gen Virol, 2002. 83(Pt 9): p. 2247-55.

68. Cheshenko, N., et al., Multiple receptor interactions trigger release of membrane and intracellular calcium stores critical for herpes simplex virus entry. Mol Biol Cell, 2007. 18(8): p. 3119-30.

69. Immergluck, L. C., et al., Viral and cellular requirements for entry of herpes simplex virus type 1 into primary neuronal cells. J Gen Virol, 1998. 79 (Pt 3): p. 549-59.

70. Nixon, B., et al., Genital Herpes Simplex Virus Type 2 Infection in Humanized HIV-Transgenic Mice Triggers HIV Shedding and Is Associated With Greater Neurological Disease. J Infect Dis, 2014. 209(4): p. 510-22.

71. Cheshenko, N., et al., HSV usurps eukaryotic initiation factor 3 subunit M for viral protein translation: novel prevention target. PLoS One, 2010. 5(7): p. e11829.

72. Carbonetti, S., et al., Soluble HIV-1 Envelope Immunogens Derived from an Elite Neutralizer Elicit Cross-Reactive V1V2 Antibodies and Low Potency Neutralizing Antibodies. PLoS One, 2014. 9(1): p. e86905.

73. Janes, H., et al., Vaccine-induced gag-specific T cells are associated with reduced viremia after HIV-1 infection. J Infect Dis, 2013. 208(8): p. 1231-9.

74. Ferre, A. L., et al., Immunodominant HIV-specific CD8+ T-cell responses are common to blood and gastrointestinal mucosa, and Gag-specific responses dominate in rectal mucosa of HIV controllers. J Virol, 2010. 84(19): p. 10354-65.

75. Schiffer J T, Corey L (2013) Rapid host immune response and viral dynamics in herpes simplex virus-2 infection. Nat Med 19:280-90.

76. Sydiskis, Schultz (1965) Herpes simplex skin infection in mice. J Infect Dis 115:237-46.

77. Nixon B et al. (2013) Griffithsin protects mice from genital herpes by preventing cell-to-cell spread. J Virol 87:6257-69.

78. Nimmerjahn F, Bruhns P, Horiuchi K, Ravetch J V (2005) FcgammaRIV: a novel FcR with distinct IgG subclass specificity. Immunity 23:41-51.

79. Wang K et al. (2015) A Herpes Simplex Virus 2 (HSV-2) gD Mutant Impaired for Neural Tropism Is Superior to an HSV-2 gD Subunit Vaccine To Protect Animals from Challenge with HSV-2. J Virol 90:562-74.

80. Boukhvalova M et al. (2015) Efficacy of the Herpes Simplex Virus 2 (HSV-2) Glycoprotein D/AS04 Vaccine against Genital HSV-2 and HSV-1 Infection and Disease in the Cotton Rat *Sigmodon hispidus* Model. J Virol 89:9825-40.

81. Yin H et al. (2013) IL-33 accelerates cutaneous wound healing involved in upregulation of alternatively activated macrophages. Mol Immunol 56:347-53.

82. Rak G D et al. (2015) IL-33-Dependent Group 2 Innate Lymphoid Cells Promote Cutaneous Wound Healing. J Invest Dermatol.

83. Anthony R M, Kobayashi T, Wermeling F, Ravetch J V (2011) Intravenous gammaglobulin suppresses inflammation through a novel T(H)2 pathway. Nature 475:110-3.

84. Simmons, Nash (1984) Zosteriform spread of herpes simplex virus as a model of recrudescence and its use to investigate the role of immune cells in prevention of recurrent disease.

85. Ligas, Johnson (1988) A herpes simplex virus mutant in which glycoprotein D sequences are replaced by beta-galactosidase sequences binds to but is unable to penetrate into cells.

86. Nixon B et al. (2013) Griffithsin protects mice from genital herpes by preventing cell-to-cell spread. Journal of virology 87:6257-69.

87. Ejercito, Kieff, Roizman (1968) Characterization of herpes simplex virus strains differing in their effects on social behaviour of infected cells. J Gen Virology 2:357-64.

88. Brown, Ritchie, Subak-Sharpe (1973) Genetic studies with herpes simplex virus type 1. The isolation of temperature-sensitive mutants, their arrangement into complementation groups and recombination analysis leading to a linkage map. The Journal of general virology 18:329-46.

89. Wan Y, Renner D W, Albert I, Szpara M L (2015) VirAmp: a galaxy-based viral genome assembly pipeline. Gigascience 4:19.

90. Larkin M A et al. (2007) Clustal W and Clustal X version 2.0. Bioinformatics 23:2947-8.

91. Tamura K, Stecher G, Peterson D, Filipski A, Kumar S (2013) MEGA6: Molecular Evolutionary Genetics Analysis version 6.0. Mol Biol Evol 30:2725-9.

92. Bologna-Molina R, Damian-Matsumura P, Molina-Frechero N (2011) An easy cell counting method for immunohistochemistry that does not use an image analysis program. Histopathology 59:801-3.

93. Ackerman M et al. (2011) A robust, high-throughput assay to determine the phagocytic activity of clinical antibody samples. Journal of Immunological Methods 366:8-19.

94. Petro C et al. (2015) Herpes simplex type 2 virus deleted in glycoprotein D protects against vaginal, skin and neural disease. Elife 4.

95. Cheshenko N et al. (2013) HSV activates Akt to trigger calcium release and promote viral entry: novel candidate target for treatment and suppression. FASEB J 27:2584-99.

96. Kolb A W, Larsen I V, Cuellar J A, Brandt C R (2015) Genomic, phylogenetic, and recombinational characterization of herpes simplex virus 2 strains. J Virol 89:6427-34.

97. Dudek T E, Torres-Lopez E, Crumpacker C, Knipe D M (2011) Evidence for differences in immunologic and pathogenesis properties of herpes simplex virus 2 strains from the United States and South Africa. J Infect Dis 203:1434-41.

What is claimed is:

1. A method of vaccinating a subject against an HSV-1 infection, the method comprising administering to the subject a recombinant herpes simplex virus-2 (HSV-2) in an amount effective to vaccinate a subject for an HSV-1 infection, wherein the recombinant HSV-2 has a deletion of the HSV-2 glycoprotein D-encoding gene in the genome thereof and comprises a herpes simplex virus-1 (HSV-1) glycoprotein D on a lipid bilayer thereof.

2. The method of claim 1, wherein the surface glycoprotein is present on a lipid bilayer thereof by way of infecting a cell with a recombinant HSV-2 having a deletion of an HSV-2 glycoprotein D-encoding gene, wherein the cell is or has been transfected to express the surface glycoprotein on a cell membrane thereof, and wherein the recombinant HSV-2 comprising the surface glycoprotein present on a lipid bilayer is produced from the cell.

3. The method of claim 1, wherein the subject is administered a subcutaneous priming dose and is administered a second dose subcutaneously or intravaginally.

4. A method of vaccinating a subject against an HSV-2 infection, the method comprising administering to the subject a recombinant herpes simplex virus-2 (HSV-2) in an amount effective to vaccinate a subject for an HSV-1 infection, wherein the recombinant HSV-2 has a deletion of the HSV-2 glycoprotein D-encoding gene in the genome thereof and comprises a herpes simplex virus-1 (HSV-1) glycoprotein D on a lipid bilayer thereof.

5. The method of claim 4, wherein the surface glycoprotein is present on a lipid bilayer thereof by way of infecting a cell with a recombinant HSV-2 having a deletion of an HSV-2 glycoprotein D-encoding gene, wherein the cell is or has been transfected to express the surface glycoprotein on a cell membrane thereof, and wherein the recombinant HSV-2 comprising the surface glycoprotein present on a lipid bilayer is produced from the cell.

6. The method of claim 4, wherein the subject is administered a subcutaneous priming dose and is administered a second dose subcutaneously or intravaginally.

7. A method of vaccinating a subject against an HSV-1 and HSV-2 co-infection, the method comprising administering to the subject a recombinant herpes simplex virus-2 (HSV-2) in an amount effective to vaccinate a subject for an HSV-1 and HSV-2 co-infection, wherein the recombinant HSV-2 has a deletion of the HSV-2 glycoprotein D-encoding gene in the genome thereof and comprises a herpes simplex virus-1 (HSV-1) glycoprotein D on a lipid bilayer thereof.

8. The method of claim 7, wherein the surface glycoprotein is present on a lipid bilayer thereof by way of infecting a cell with a recombinant HSV-2 having a deletion of an HSV-2 glycoprotein D-encoding gene, wherein the cell is or has been transfected to express the surface glycoprotein on a cell membrane thereof, and wherein the recombinant HSV-2 comprising the surface glycoprotein present on a lipid bilayer is produced from the cell.

9. The method of claim 7, wherein the subject is administered a subcutaneous priming dose and is administered a second dose subcutaneously or intravaginally.

* * * * *